(12) United States Patent
Actis

(10) Patent No.: US 8,336,404 B2
(45) Date of Patent: Dec. 25, 2012

(54) BALE SAMPLER

(75) Inventor: Bradley P. Actis, Clovis, CA (US)

(73) Assignee: H.W.J. Designs for Agribusiness, Inc., Clovis, CA (US)

( * ) Notice: Subject to any disclaimer, the term of this patent is extended or adjusted under 35 U.S.C. 154(b) by 765 days.

(21) Appl. No.: 12/360,025

(22) Filed: Jan. 26, 2009

(65) Prior Publication Data

US 2009/0188332 A1    Jul. 30, 2009

Related U.S. Application Data

(60) Provisional application No. 61/023,812, filed on Jan. 25, 2008.

(51) Int. Cl.
*G01N 1/04* (2006.01)
(52) U.S. Cl. ............... 73/864.42; 73/864; 73/864.41
(58) Field of Classification Search ............... 73/864.41, 73/864.42
See application file for complete search history.

(56) References Cited

U.S. PATENT DOCUMENTS

| | | | |
|---|---|---|---|
| 2,131,502 A * | 9/1938 | Elliot | ............................. 100/80 |
| 2,459,383 A | 1/1949 | Levy | |
| 3,034,358 A | 5/1962 | Young et al. | |
| 3,146,654 A | 9/1964 | Mathews et al. | |
| 3,464,298 A | 9/1969 | Roach | |
| 5,178,020 A * | 1/1993 | Elam et al. | .................. 73/864.42 |
| 6,386,026 B1 * | 5/2002 | Zamfes | ...................... 73/152.04 |

FOREIGN PATENT DOCUMENTS

KR    10-2002-17581 A    3/2002

OTHER PUBLICATIONS

International Search Report mailed Apr. 28, 2009 from corresponding International Application No. PCT/US2009/032064, filed Jan. 26, 2009 (7 pages).
Written Opinion mailed Apr. 28, 2009 from corresponding International Application No. PCT/US2009/032064, filed Jan. 26, 2009 (4 pages).

* cited by examiner

*Primary Examiner* — Hezron E Williams
*Assistant Examiner* — Paul West
(74) *Attorney, Agent, or Firm* — Klein, O'Neill & Singh, LLP

(57) ABSTRACT

A system for sampling a bale of fibrous material is provided including a transportation mechanism for moving the bale from a first point to a second point and a first gripper for obtaining a sample from the bale when the bale is at a position between the first point and the second point. The gripper includes a movable finger for gripping the sample from the bale. An actuator comprising an actuating rod is provided for pushing the sample away from the movable finger.

18 Claims, 23 Drawing Sheets

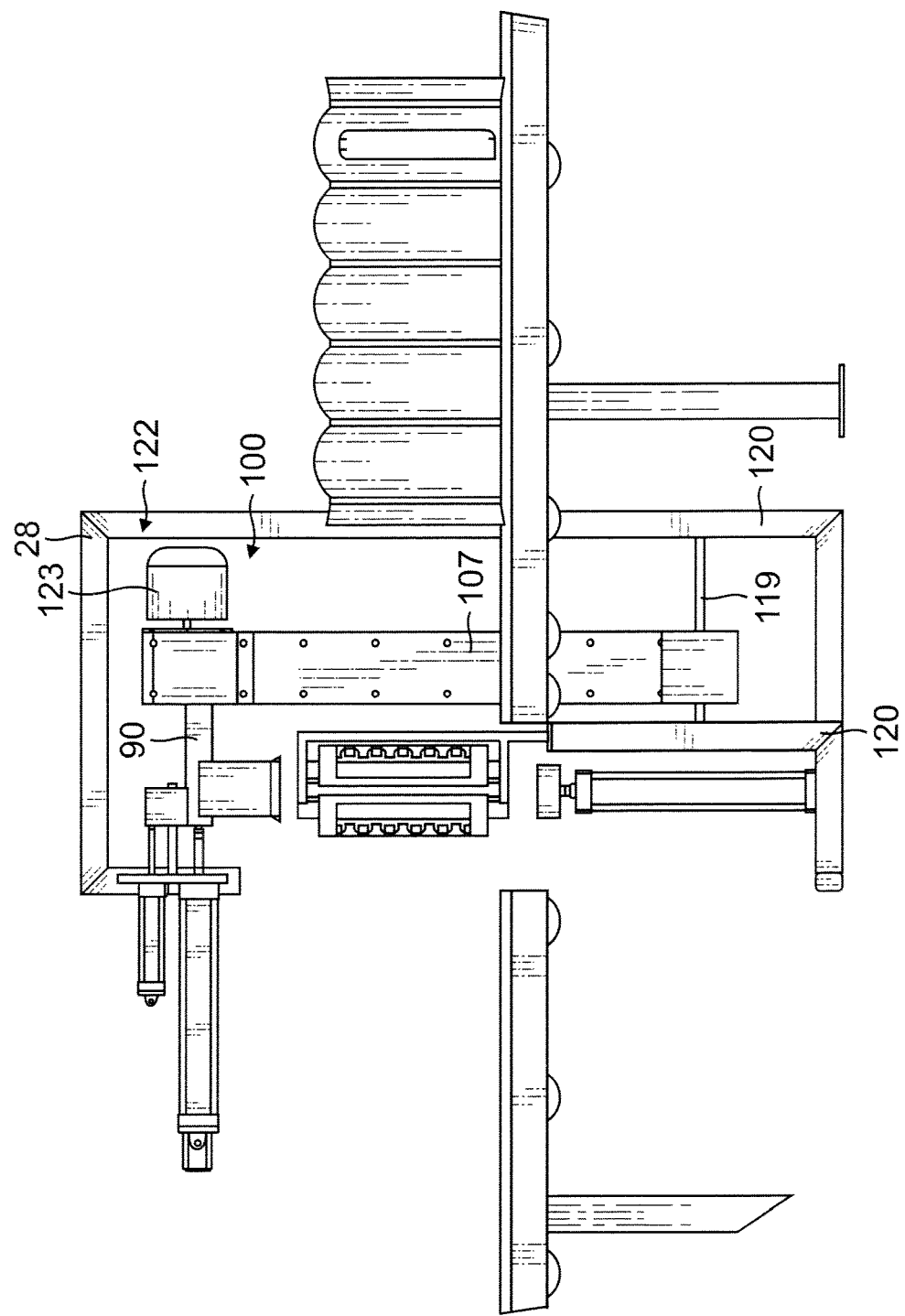

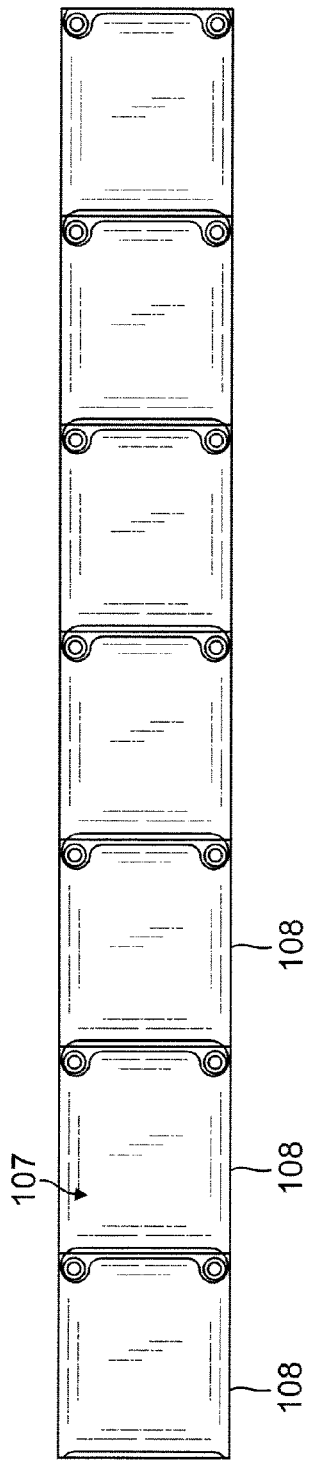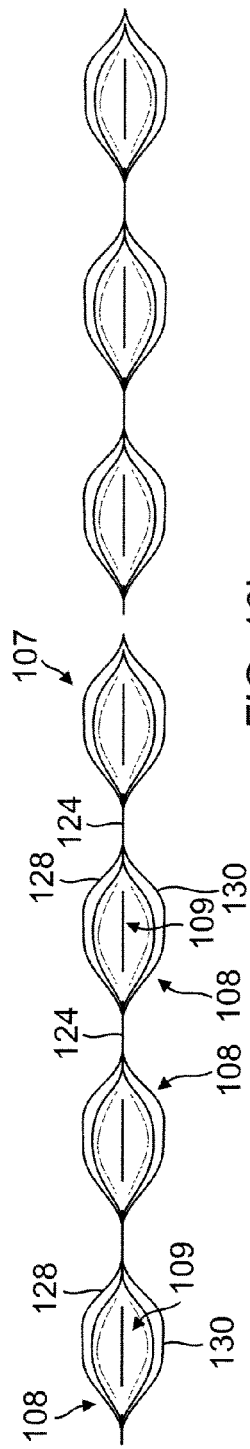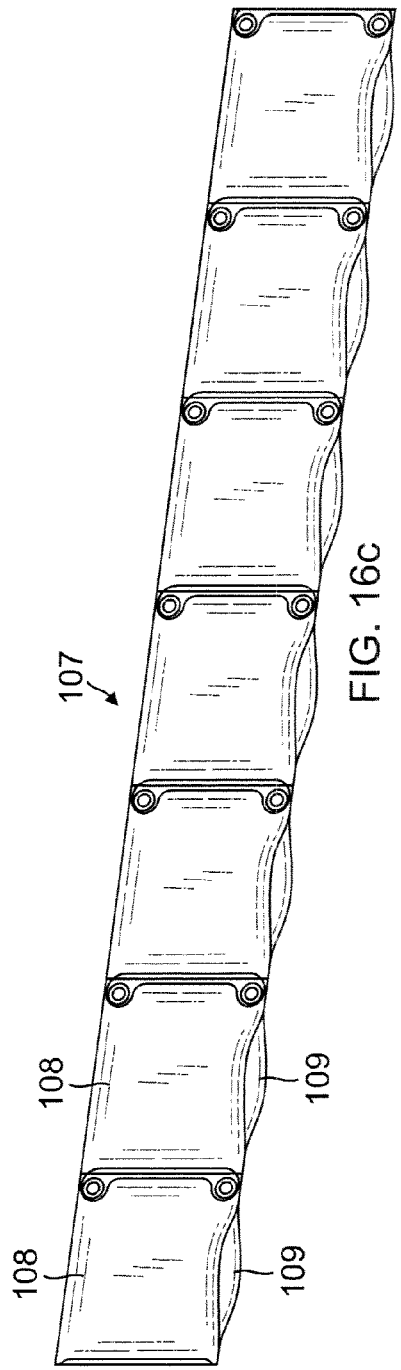

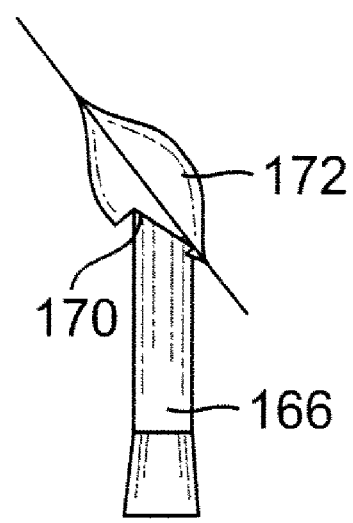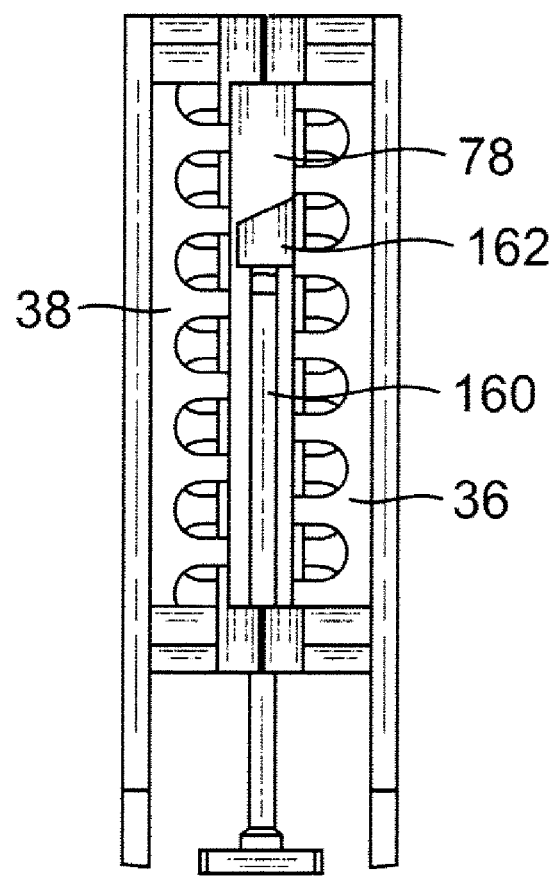
FIG. 19

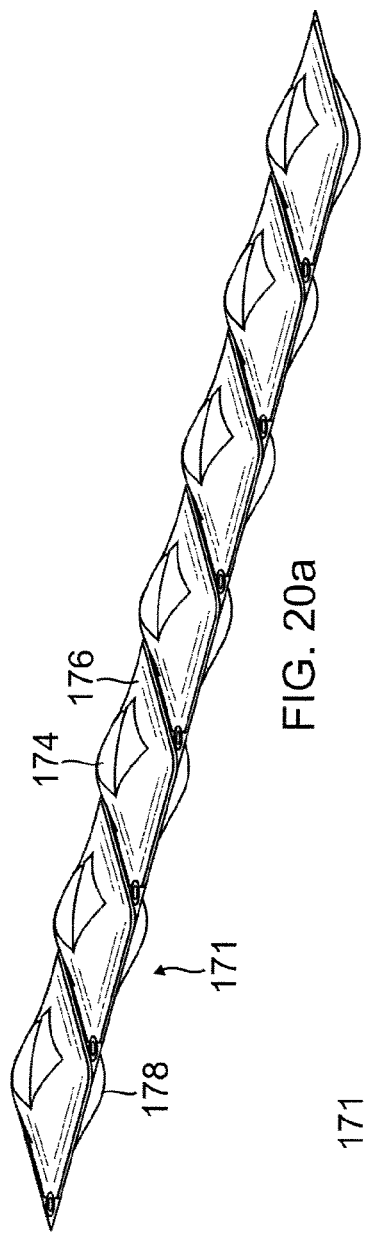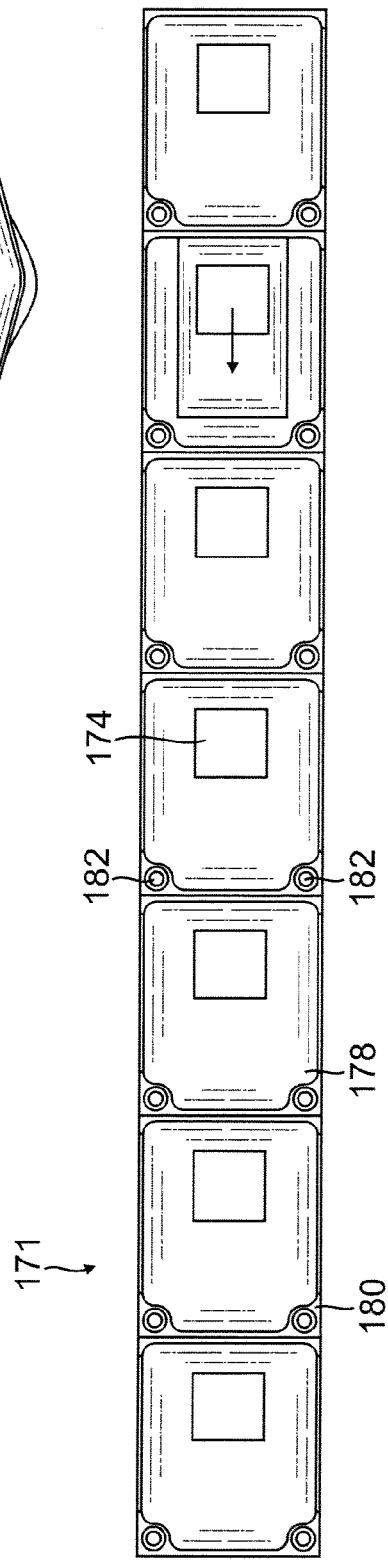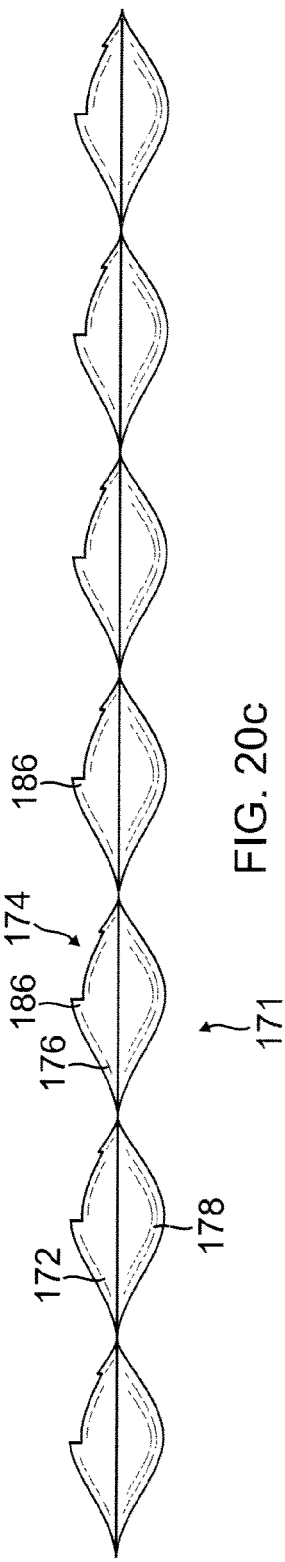

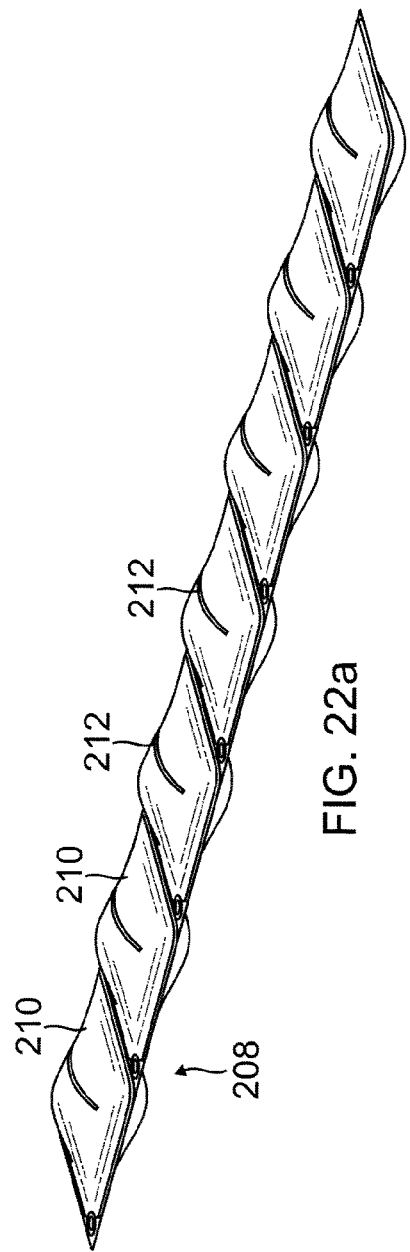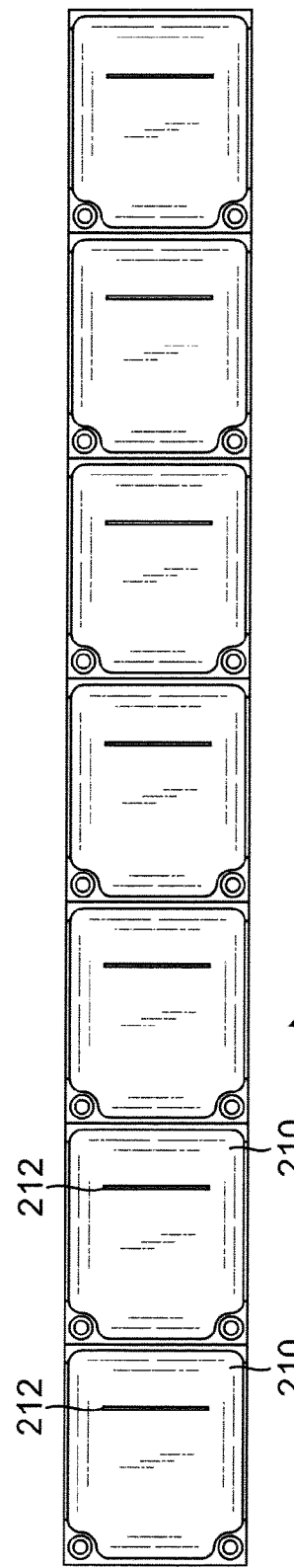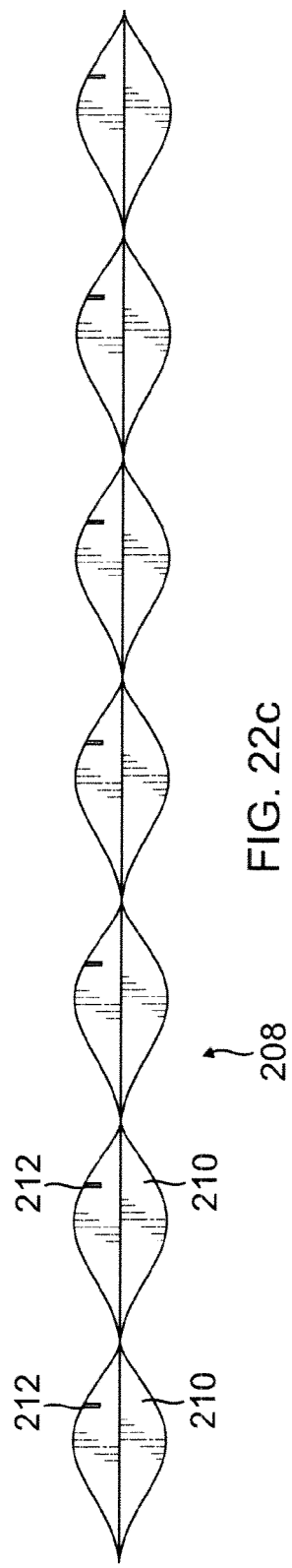

BALE SAMPLER

CROSS-REFERENCE TO RELATED APPLICATION

This is a Regular Utility application of Provisional Application Ser. No. 61/023,812, filed Jan. 25, 2008, the contents of which are expressly incorporated herein by reference.

BACKGROUND

In order to evaluate the quality of certain fibrous materials, such as cotton, before sale, a sample of the material from each bale is provided to an evaluating agency, typically a division of the USDA. This evaluation called 'grading' allows a bale, such as cotton, to be sold to customers without the entire product being seen. Further, before large quantities of the fibrous materials are stored for later sale, samples of the material may be obtained to be provided to perspective customers for testing, rather than transporting an entire bale to the perspective customer. In addition to facilitating the testing of a larger amount of material, obtaining samples from bales before the bales are bagged or otherwise encased in a protective covering ensures that the integrity of such protective covering remains intact. A sample is usually formed during the pressing process using a cutting protrusion (typically about ¾ inch high) on the pressing surface or surfaces, typically in a U shape. This cutting protrusion is forced into the fibers, severing them from the cohesive, intertwined body of the bale. Since the sample will be removed, it is practical to cut the sample between the areas where bale retention straps are typically placed. The cut sample will typically bulge from the side of the bale when the pressing force is removed since it is not bound to its neighboring fibers contained by bale retention straps. The sample generally retains an "uncut" side across a top length after the sample is cut with the aforementioned U-shaped cutter to retain the sample on the bale. Conventional methods for obtaining a sample from every bale requires intense manual labor with workers having to physically tear one or more samples, typically two, of material from the same bale and insert them into a bag or sleeve. In certain applications, a generally U-shape cutter is used to pre-cut a sample during a bale pressing and forming process for later manual removal by a worker. Not only are workers prevented from completing other tasks while they are obtaining samples, but repeating the same motion for long periods of time may lead to chronic injuries. Further, manually obtaining the samples increases the likelihood that the resulting samples will be nonuniformly sized, will be contaminated by substances on the workers hands, and will be more costly due to the added labor expense.

SUMMARY

A system for sampling a bale of fibrous material is provided including a transportation mechanism for moving the bale from a first point to a second point and a first gripper for obtaining a sample from the bale when the bale is at a position between the first point and the second point. The gripper includes a movable finger for gripping the sample from the bale. An actuator comprising an actuating rod is provided for pushing the sample away from the movable finger.

A further aspect of the present invention includes a method for sampling a bale of fibrous material. The method comprises cutting a section of the bale, the section providing a sample to be collected, and moving the bale from a first point to a second point. Further, the method includes moving a first gripper against the bale, moving a finger on the first gripper to grasp the cut section of the bale, separating the cut section from the bale, and transferring the cut section into a collection device.

A further aspect of the present invention includes a bag assembly of collection bags for bagging fibrous samples. The bag assembly comprises a first bag comprising two opposing sheets having at least four sealed edges to define an interior cavity and a second bag comprising two opposing sheets having at least four sealed edges to define an interior cavity. The second bag is removably connected to at least one of the four sealed edges of the first bag. The bag assembly further includes a perimeter defining an opening on at least one of the two opposing sheets of the first bag and a perimeter defining an opening on at least one of the two opposing sheets of the second bag.

BRIEF DESCRIPTION OF THE DRAWINGS

FIG. 11a is a side view of the bale sampler of FIG. 1 having a bag supply and rotator assembly attached thereto.

FIG. 11b is an orthogonal view of the bag supply and rotator assembly of FIG. 11a.

FIGS. 16a, 16b, and 16c are a top, side, and orthogonal views, respectively, of an exemplary bag supply in accordance with aspects of the present invention.

FIGS. 18 and 19 are schematic side views of another exemplary bagging assembly according to aspects of the present invention.

FIGS. 20a, 20b, and 20c are a top, side, and orthogonal views, respectively, of another exemplary bag supply in accordance with aspects of the present invention.

FIGS. 22a, 22b, and 22c are a top, side, and orthogonal views, respectively of still another exemplary bag supply in accordance with aspects of the present invention.

DETAILED DESCRIPTION

Figure 1:
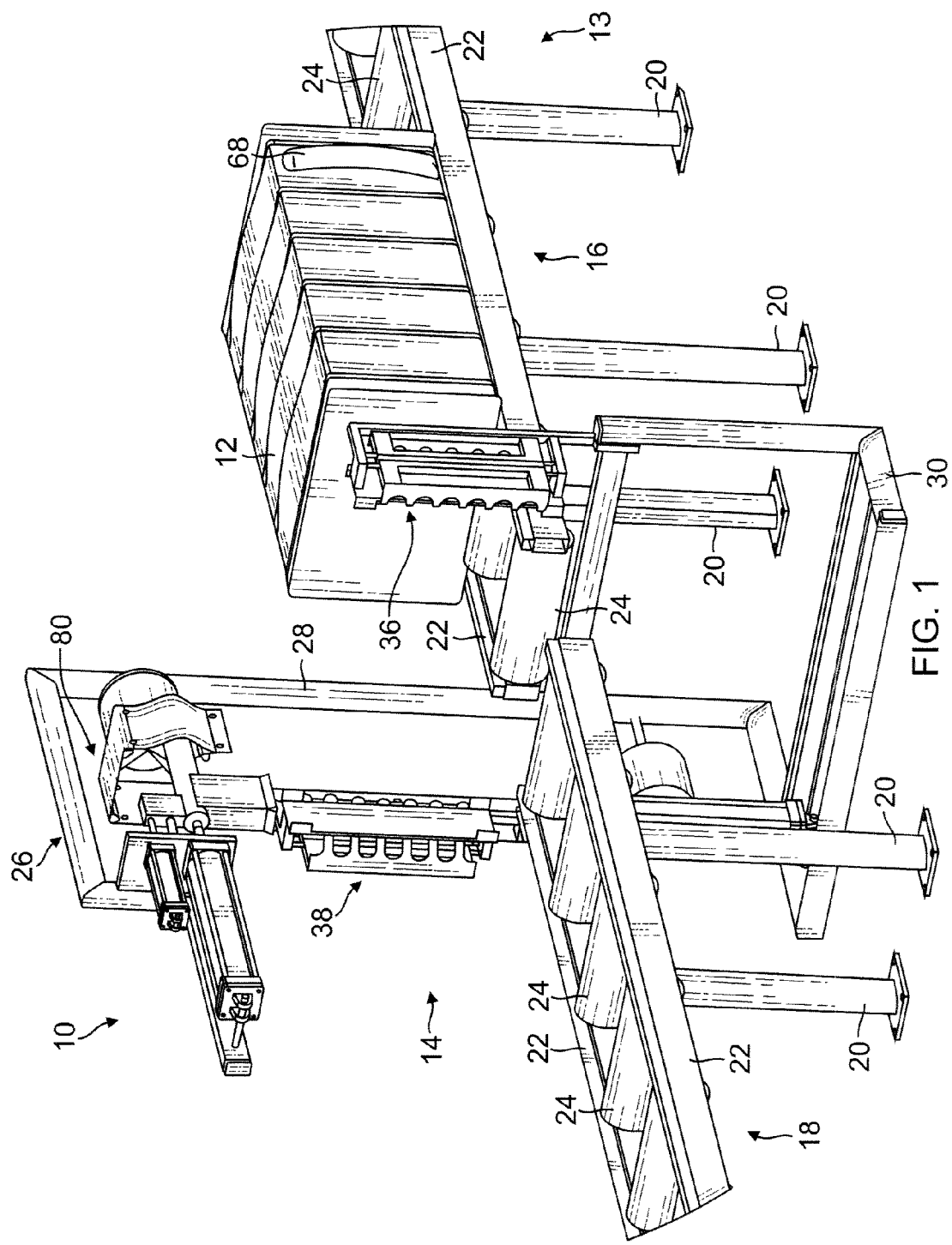
FIG. 1 is an orthogonal view of an exemplary bale sampler according to aspects of the present invention.

With reference to FIG. 1, a bale sampler 10 in accordance with exemplary embodiments of the present invention is provided to obtain and package samples of a fibrous substance from a bale 12. More specifically, the bale sampler 10 can automatically obtain a sufficiently and relatively uniformly sized sample from both sides of the bale 12 of a fibrous substance at nearly any location along the bale and, if desired, insert the two samples into a bag or two separate bags. In other embodiment, only a single sample or more than two samples are be taken from the bale.

As shown in FIG. 1, the bale sampler 10 generally comprises a bale transport mechanism or conveyor 13, a sampling assembly 14, and a bagging assembly 80. The conveyor 13 may comprise a first conveyor 16 and a second conveyor 18 located on either side of the sampling assembly 14, as will be described in more detail below. Since the first and second conveyors 16, 18 are substantially identical, only the first conveyor will be described in detail. The first conveyor 16 comprises legs 20 for supporting a set of rails 22 and a plurality of spaced rotatable cylinders 24 extending between the rails 22. The cylinders 24 are configured such that a portion of each cylinder is substantially flush with or protrudes slightly above the rails 22, allowing a bale 12 located on the conveyor 13 to be transported in the direction of rotation of the cylinders. One of ordinary skill in the art will appreciate that the conveyor 13 may also be in the form of a conveyor belt driven by a rotatable source, such as a motor or a drive train, a table with an external pushing arm, or another appropriate configuration to transport a bale 12.

With further reference to FIG. 1, the sampling assembly 14 comprises a frame 26 having a generally U-shaped configuration having two vertical frame portions 28, for supporting rail of the sampling assembly 14 and a bagging assembly 80, and a horizontal frame portion 30 for supporting first and second grippers 36, 38 and to position the first gripper 36 on a far side of the bale 12, as will be described in more detail below. As will be appreciated by one of ordinary skill in the art, the frame may have various configurations while remaining within the scope and spirit of the present invention.

Figure 2:
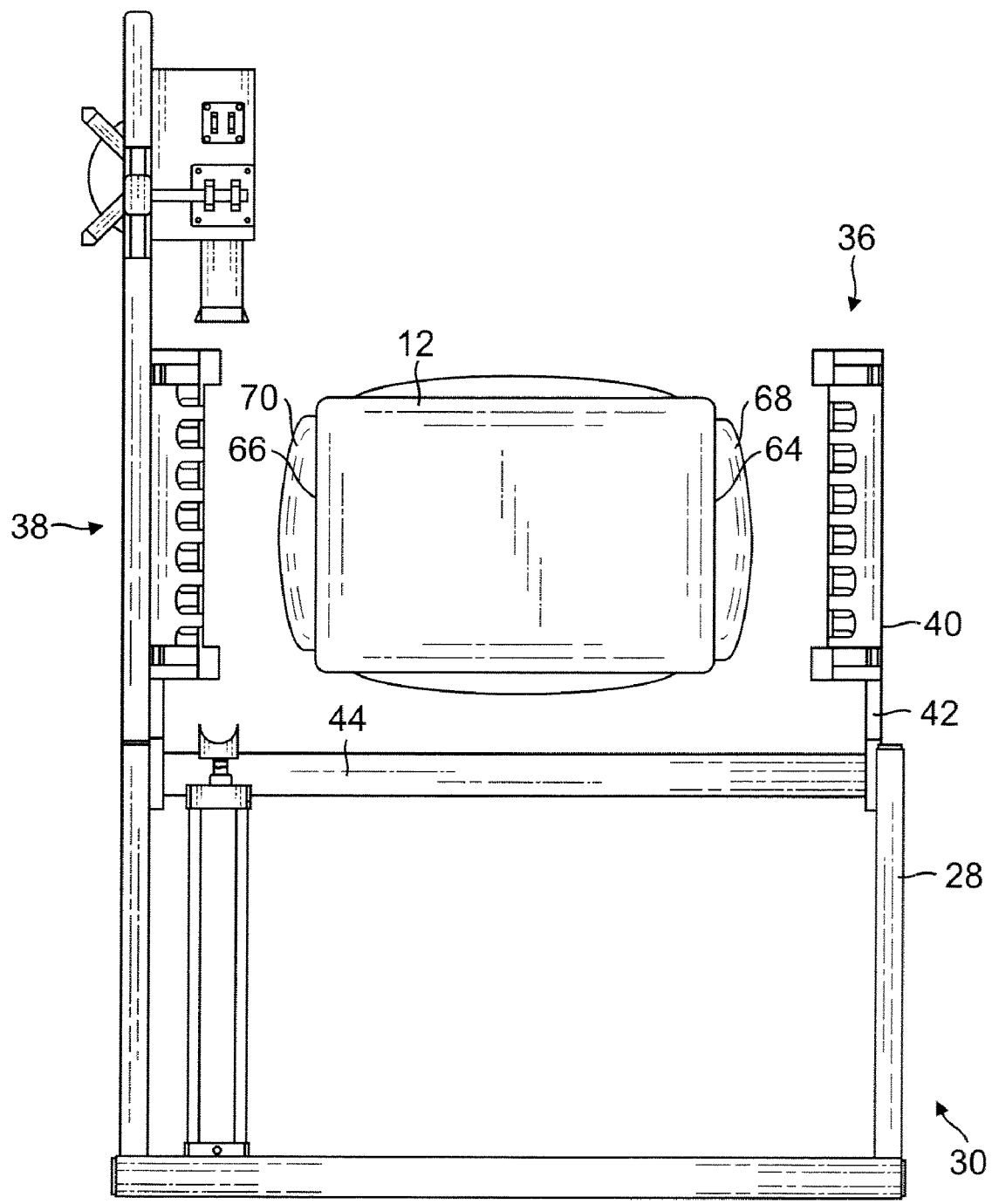
FIG. 2 is an end view of the bale sampler of FIG. 1.
Figure 3:
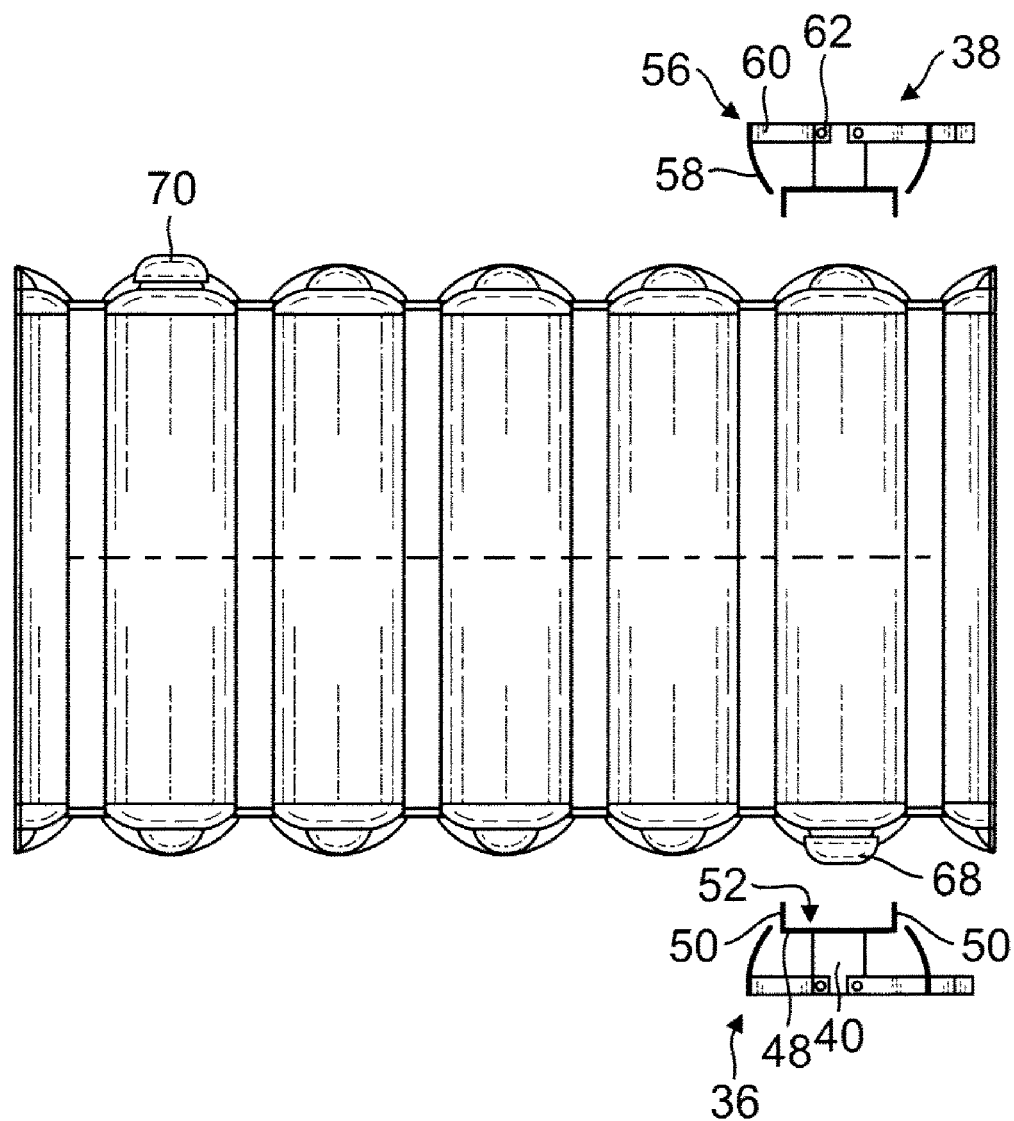
FIG. 3 is a top schematic view of a sampling assembly of the bale sampler of FIG. 1 with first and second grippers in an open position.

With reference now to FIGS. 2 and 3, the sampling assembly 14 comprises the first gripper 36 and the second gripper 38 with each gripper adapted to remove a sample from a respective side of the bale 12 on the conveyor 13 (FIG. 1). For clarity, the conveyor 13 is not shown in FIG. 2 or 3. The first and second grippers 36, 38 face each other and have a substantially similar configuration. Therefore, only the first gripper 36 will be described in detail and it will be appreciated that the second gripper 38 will have substantially similar features. The first gripper 36 comprises a base 42 movably mounted on a track 44 traversing the two vertical frame portions 28 and extends generally parallel to the horizontal frame portion 30. In one exemplary embodiment, the base 42 has a through hole through which the track 44 extends, thereby allowing the first gripper 36 to slide along the track 44. A spine 40 extends vertically from the base 42, the spine supporting a sample bay 46 (FIG. 3) centrally disposed along a longitudinal axis of the spine. The sample bay 46 comprises a base wall 48 and two side walls 50 extending from the base wall to form a generally U-shaped channel 52 for receiving and collecting a sample of fibrous material.

Figure 4:
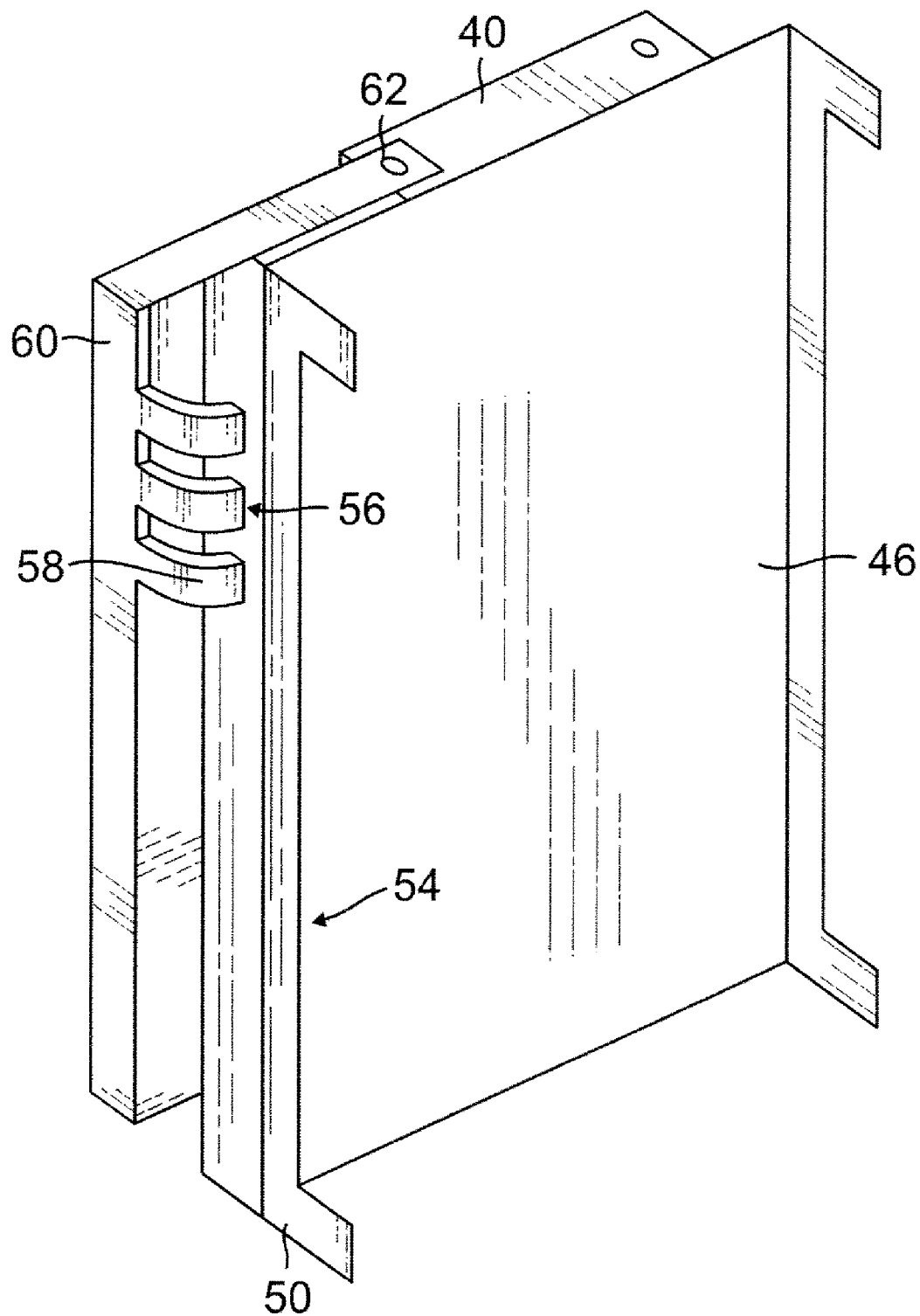
FIG. 4 is a schematic orthogonal view of an exemplary gripper according to aspects of the present invention.

With reference now also to FIG. 4, the side walls 50 are dimensioned to allow fingers 56 to pass therethrough, and, in one exemplary embodiment, the side walls have a cut-away section 54 through which the fingers 56 can pass. Thus, in the embodiment shown, the side walls 50 are generally U-shaped in configuration. Each gripper 36, 38, with only one shown in FIG. 4, has two sets of fingers 56 extending along opposite sides of the sample bay 46. In one exemplary embodiment, the fingers 56 on opposing sides of the gripper 36 alternate such that in an engaged position, as described in more detail below, the fingers sequentially receive adjacent fingers similar to the manner in which the fingers on two hands of a person clasp together. Viewed more broadly, the fingers each have an edge for moving against a sample to grip the sample. In a particular embodiment, two opposing edges, such as from two sets of fingers, are configured to edge a sample therebetween to grip the sample.

The fingers 56 have an arcuate section 58 extending from a base section 60 and are rotatably secured to the spine 40 by pins 62 to allow them to be moved between an open position and the engaged position. In the open position, as shown in FIG. 3, the fingers 56 permit the sample bay 46 of the grippers 36, 38 to abut a sampling section of the bale 12 such that a sample may be taken. In one exemplary embodiment, in the open position the base section 60 of the fingers 56 is generally parallel to the base wall 48 of the sample bay 46 and the arcuate section 58 does not protrude through the cut away section 54. In the engaged position (FIG. 5), the fingers 56 are rotated radially towards the sample bay 46 such that the arcuate section 58 of each finger 56 penetrates the cut away section 54 and forms a generally enclosed area with the base wall 48 of the sample bay to house a sample, as will be described in more detail below. The present bale sampler 10 is configured to grab two samples from sides of a strapped bale that have been pre-cut during the pressing process. However, as presently contemplated, the cuts may be performed by the bale sampler 10 as taught elsewhere herein.

The operation of obtaining a sample using the sampling assembly 14 will now be described. As shown in FIGS. 1 and 2, the strapped bale 12 is positioned on the rotating cylinders 24 of the first conveyor 16. The bale 12 has a first side 64 having a pre-cut section 68 from which a sample may be taken and a second side 66 also having a pre-cut section 70 from which a sample may be taken. The pre-cut section may be performed manually or by sending the bale through a set of cutters designed to cut the bale as the bale moves on by. Since the bale is compressed and strapped, the fibrous material is under relatively high pressure. As such, the pre-cut sections 68, 70 tend to protrude from the sides 64, 66, respectively, allowing them to be grasped and separated from the bale 12, as will be described in more detail below. As the rotating cylinders 24 transport the bale 12 toward the sampling assembly 14, but before the bale reaches the sampling assembly, the first gripper 36 is moved along the track 44 such that the sample bay 46 of the first gripper faces the first side 64 of the bale 12 (FIG. 2).

The bale 12 is advanced along the first conveyor 16 until the pre-cut section 68 of the first side 64 is generally aligned with the first gripper 36 (FIG. 3), the first gripper having its fingers 56 in the open position. Bales of fibrous material are generally uniform by design to facilitate shipment, storage and usage, and therefore, a cut sample will be located in substantially the same place on each bale. Using object detection sensors, or conveyor control, or other devices commonly used for positioning the bale is stopped with the sample generally aligned with the relevant gripper. When the pre-cut section 68 is aligned with the first gripper 36, the second gripper 38 faces and is spaced from the second side 66 of the bale 12.

Figure 5:
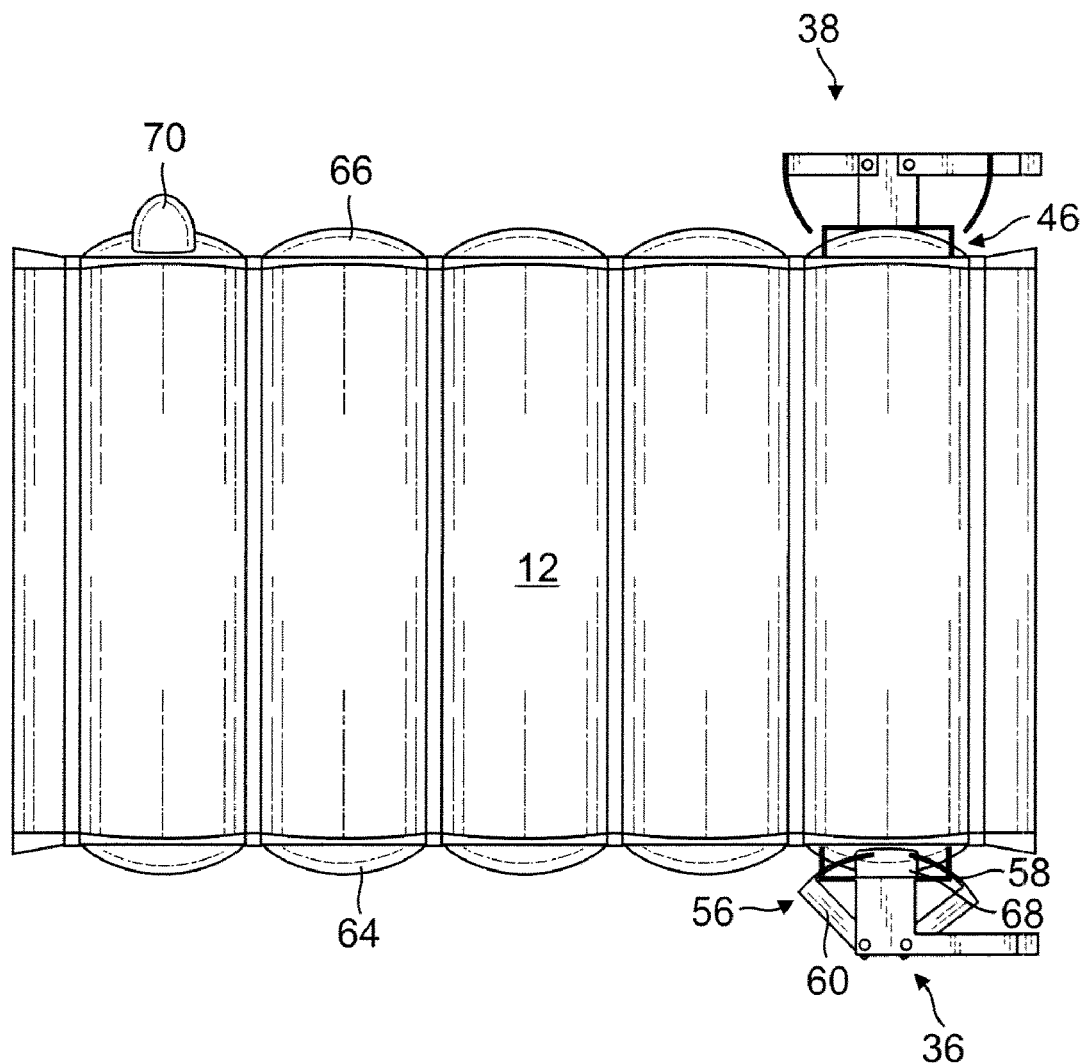
FIG. 5 is a top schematic view of a sampling assembly of the bale sampler of FIG. 1 with one gripper in a closed position and another gripper in an open position.

With reference now to FIG. 5, the first gripper 36 is then advanced toward the first side 64 of the bale 12 such that the base wall 48 of the sample bay 46 abuts or is proximate to the pre-cut section 68. Simultaneously, the second gripper 38 is advanced toward the second side 66 of the bale 12 such that the base wall 48 of the sample bay 46 abuts the second side and acts as a "backstop," preventing lateral movement of the bale on the first conveyor 16. When both grippers 36, 38 are abutting the bale 12, the fingers 56 of the first gripper 36 are moved from the open position to the engaged position, thereby grasping and removing, such as by severing or by cutting, the fibrous material protruding from the pre-cut section 68, and trapping the material between the arcuate section 58 of the fingers 56 and the sample bay 46 to obtain a first sample 72. Subsequently both grippers 36, 38 retreat from the bale 12, and the bale is advanced by the rotating cylinders 24 until the pre-cut section 70 on the second side 66 of the bale is generally aligned with the second gripper 38.

Figure 6:
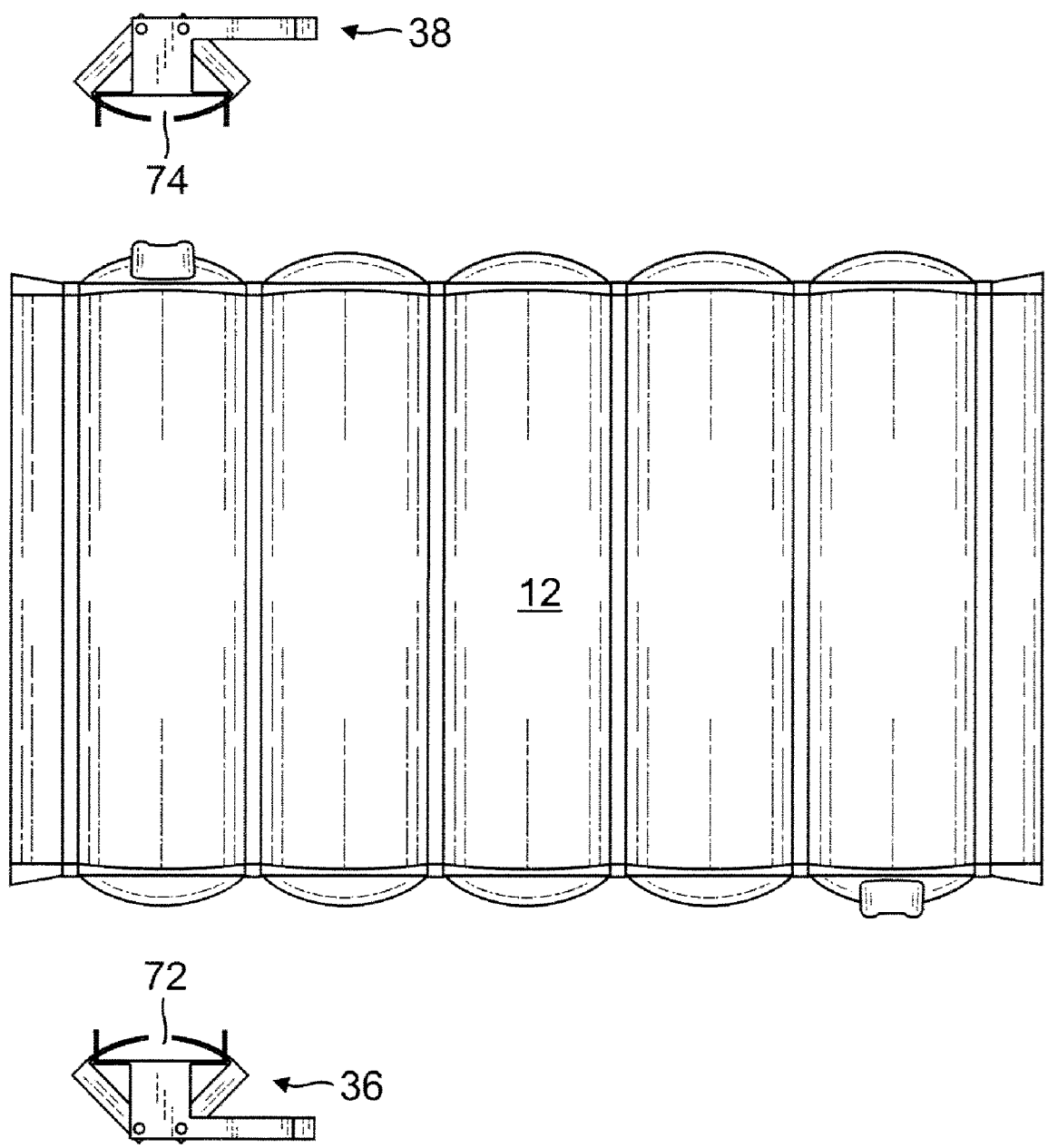
FIG. 6 is a top schematic view of a sampling assembly of the bale sampler of FIG. 1 with first and second grippers in a closed position.

Similarly to the sample-taking process described above with respect to the first sample 72, both grippers 36, 38 are attain advanced toward the bale 12, and the fingers 56 on the second gripper are moved from the open position to an engaged position to obtain a second sample 74 between the arcuate section 58 and the base wall 48 of the sample bay 46 of the second gripper, as shown in FIG. 6. It is noted that the first gripper 36 remains in the engaged position while acting as a backstop for the second gripper 38 such that the first gripper retains the first sample 72. In another exemplary embodiment, a bale sampler is provided that is movable to be aligned with a stationary bale, rather than the bale being moved. It will be appreciated by one of ordinary skill in the art that such a sliding or index unit would pose no significant technical issues.

Figure 7:
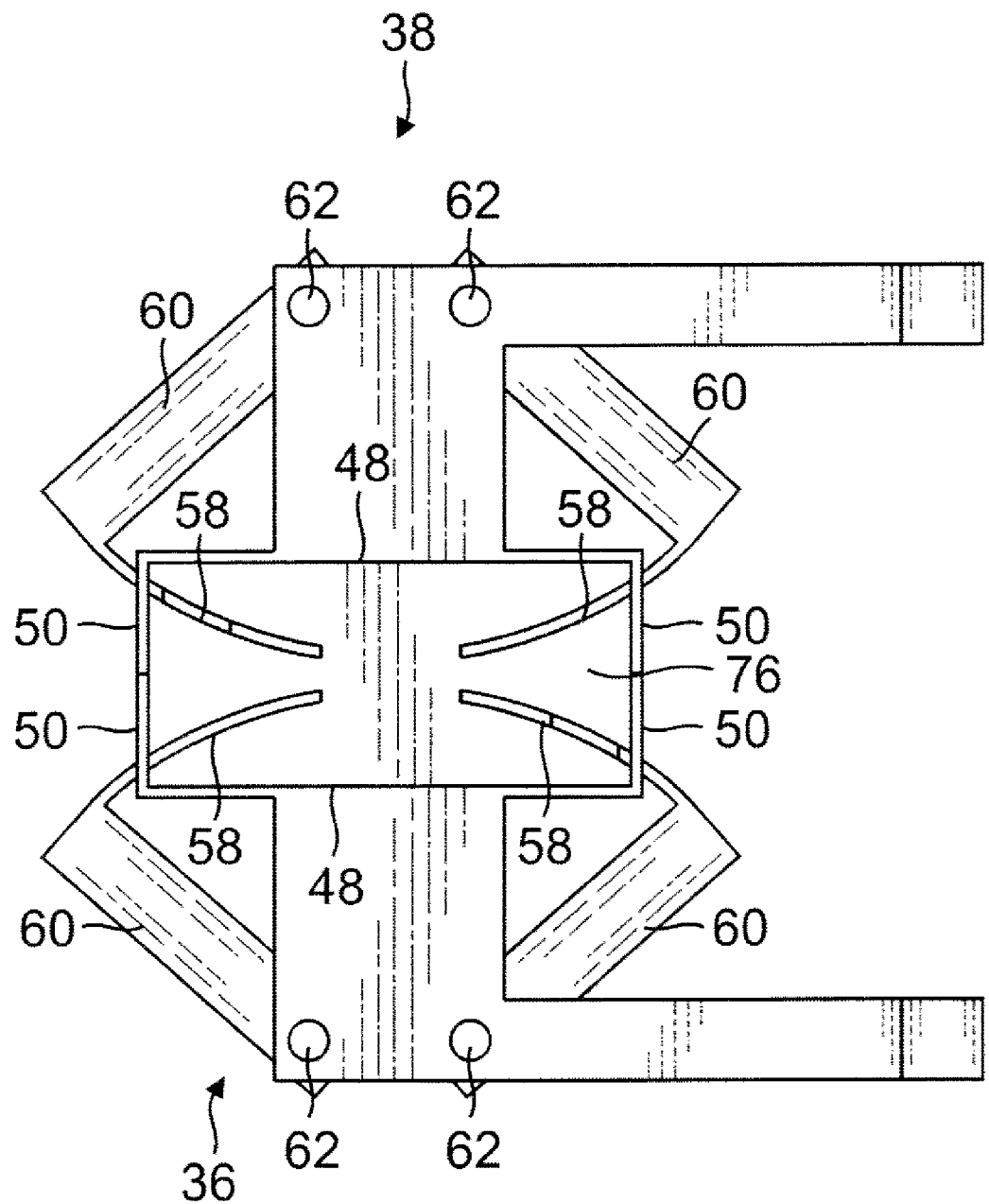
FIG. 7 is a top schematic view of the first and second grippers of FIG. 6 abutting each other in a closed position.
Figure 8:
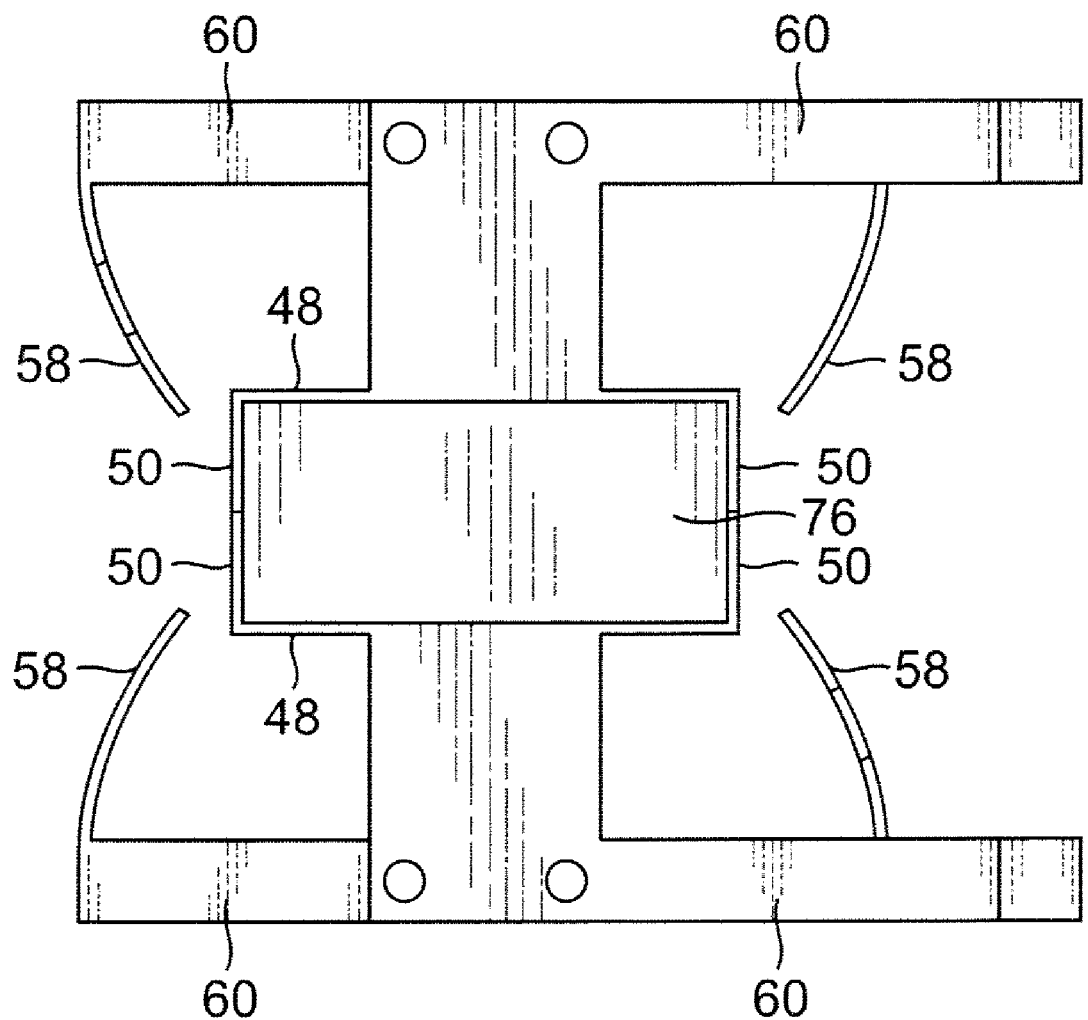
FIG. 8 is a top schematic view of the first and second grippers of FIG. 6 abutting each other in an open position.
Figure 9:
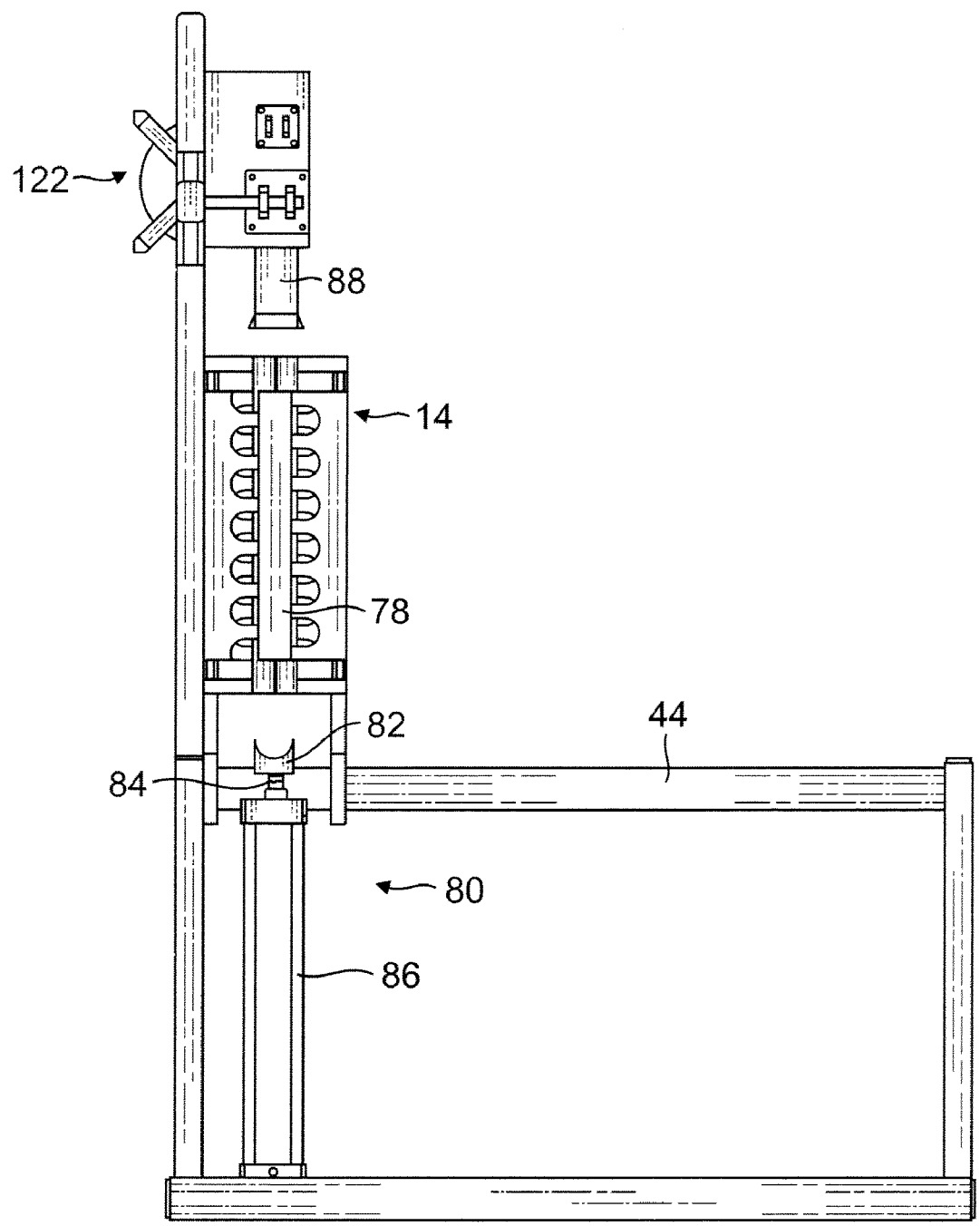
FIG. 9 is an end view of the bale sampler of FIG. 1 showing the first and second grippers abutting each other and in the open position.

After the first and second samples 72, 74 have been obtained, the two grippers 36, 38 are backed away from the bale (FIG. 6) and the rotating cylinders 24 advance the bale 12 from the first conveyor 16 onto the second conveyor 18 such that the bale may be placed in a protective bag or otherwise further processed. With reference now to FIGS. 7-9, after the bale has passed the sampling assembly 14, the two samples are brought together. In one exemplary embodiment, the first gripper 36 is advanced toward the second gripper 38 along the horizontal track 44 such that the side walls 50 of each sample bay 46 are abutting (FIG. 7). Then, the fingers 56 are moved from the engaged position to the open position, disengaging the arcuate portions 58 from the sample bay 46 and combining the two samples 72, 74 into a single combined sample 76 (FIG. 8). However, because of the nature of fibrous materials, the two samples do not fuse or substantially blend, and when necessary, can separate along the joined plane.

Figure 10:
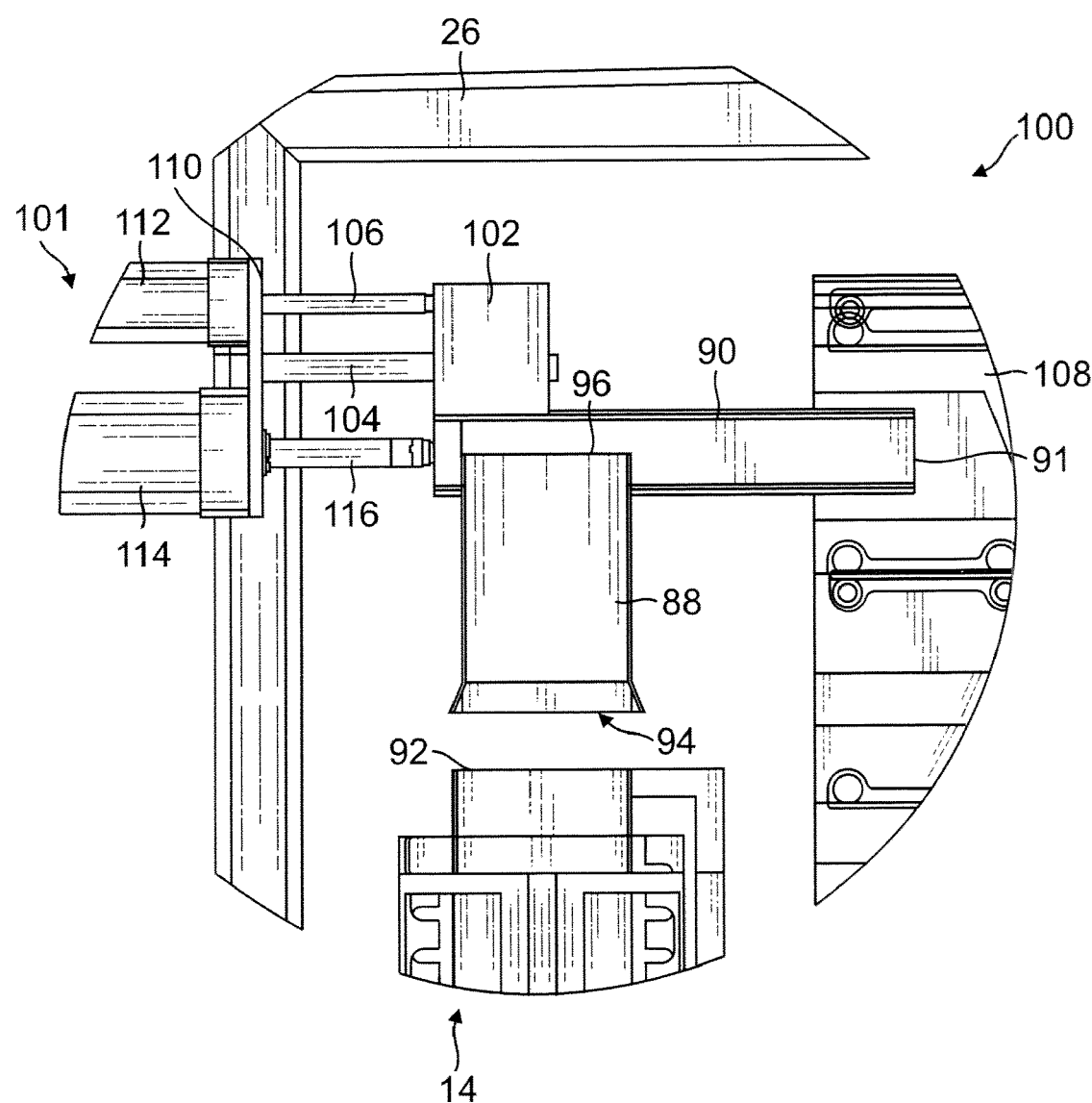
FIG. 10 is a detail view of a bagging assembly of the bale sampler of FIG. 1.

For clarity, from this point forward, the combined sample 76 will be referred to as simply "the sample," and it will be understood that the sample comprises the first sample 72 and the second sample 74. With reference to FIG. 9, the two grippers 36, 38 are located such that a channel 78 formed by the sample bays 46 containing the sample 76 is aligned with a bagging assembly 80 for removing the sample-from the sampling assembly 14 and inserting the sample into a sample bag, as described in more detail below. With reference to FIG. 10 in addition to FIG. 9, the bagging assembly 80 comprises an actuator rod 84 having an actuator head 82 at a distal end thereof for pushing the sample 76 out of the sample bay 46, through a receiving cylinder 88, and into a loading tube 90. In one exemplary embodiment, the actuator head 82 may have a concave or scoop configuration to match a curvature of the loading tube 90 to ensure that the entire sample 76 is pushed into the loading tube. However, a flat profile, like a small block, may be adequate for performing the pushing function. In one exemplary embodiment, the actuator rod 84 and actuator head 82 are moved by a rod actuator 86, such as a pneumatic or hydraulic cylinder. Moreover, one of ordinary skill in the art will appreciate that other mechanisms, such as a motor, may be used to drive the actuator head 82, and that the actuator head may be located above or next to the sample 76, depending on the orientation of the sampling assembly 14, without departing from the spirit and scope of the invention. Additionally, non-mechanical means, such as a blast of air, may be used to move the sample 76 into the loading tube 90. In another exemplary embodiment, the channel 78 is sized such that the base walls 48 of the sample bays 46 on grippers 36, 38 do not cause an appreciable compression of the sample 76, allowing the sample to exit the channel 78 by the force of gravity when the fingers 56 are moved to the open position.

With reference to FIG. 10, the receiving cylinder 88 is spaced from an open top end 92 of the sampling assembly 14. The receiving cylinder 88 has a flared input end 94 facing the open top end 92 of the sampling assembly 14 and an open output end 96 connected to the loading tube 90 to allow the sample 76 to be pushed into the receiving cylinder 88 from the sampling assembly, and from the receiving cylinder into the loading tube. The loading tube 90, dimensioned to receive and hold a sample 76 from the receiving cylinder 88, is positioned generally orthogonal to the receiving cylinder 88 having an output end 91 for transferring the sample to a bag 108, as described below. The loading tube 90, having the receiving cylinder 88 attached thereto is movable relative to a bag assembly 100, and in one exemplary embodiment, is mounted on an actuator assembly 101 for moving a sample from the loading tube to a bag 108 of the bag assembly 100.

Figure 15:
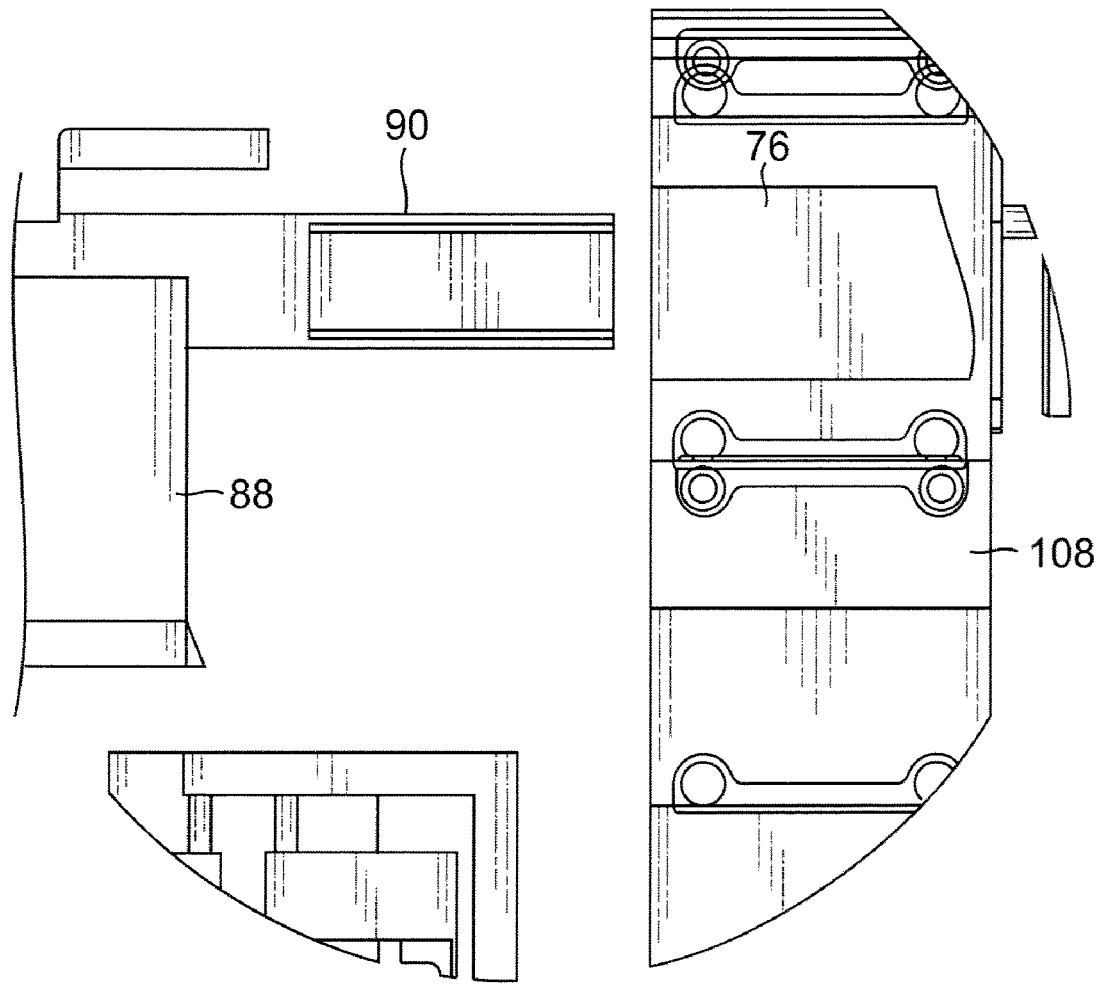
FIG. 15 is a schematic partially cutaway detail view of a bagged sample.

With continued reference to FIG. 10, the actuator assembly 101 comprises a base 110 for supporting a loading tube actuator 112 and a loading rod actuator 114. A movable link 106 connects the base 110 to a chassis 102 attached to the loading tube 90, the movable link being transferable between an extended position and a retracted position. More specifically, the chassis 102 is located above the loading tube 90 and is slidingly connected to a rail 104 extending from the base 110 such that the loading tube actuator 112, which in one exemplary embodiment is a pneumatic cylinder, can move the link 106 between the extended position (FIG. 10) and the retracted position (FIG. 15). When the link 106 is in the extended position, the loading tube 90 extends into a bag 108 on the bag assembly 100 and the receiving cylinder 88 is aligned with the top end 92 of the sampling assembly 14. When the link is in the retracted position, the loading tube 90 is spaced from the bag 108, thereby allowing the bag assembly 100 to move relative to the loading tube 90, as described in more detail below.

A loading rod 116 having a loading head 118 (FIG. 13) mounted on an end thereof is aligned with the loading tube 90 and extends front the base 110 in the same direction as the link 106. More specifically, the loading head 118 is slidably engaged with an interior surface of the loading tube 90 for pushing a sample within the loading tube into the bag 108, as described in more detail below. A loading rod actuator 14 moves the loading rod 116 between an extended position, in which the loading head 118 is proximate the output end 91 of the loading tube 90, and a retracted position, in which the loading head is proximate the base 110. The loading rod 116 may also rest in an intermediate position in which the loading rod is within the loading tube 90, but does not overlap the open output end 96 of the receiving cylinder 88, and is not proximate to the base 110 (FIG. 10). The link 106 and the loading rod 116 may be synchronized such that when the link 106 is moved between the extended position and the retracted position, the loading rod remains positioned within the loading tube 90, but does not overlap the open output end 96 of the loading tube. In one exemplary embodiment, the loading rod actuator 114 is a pneumatic cylinder. Although the loading tube actuator 112 and the loading rod actuator 114 are described as pneumatic cylinders, one of ordinary skill in the art will appreciate that other devices, such as a motor and/or a gear system, could be used to move the link 106 and loading rods 116 without departing from the spirit and the scope of the present invention.

Figure 11B:
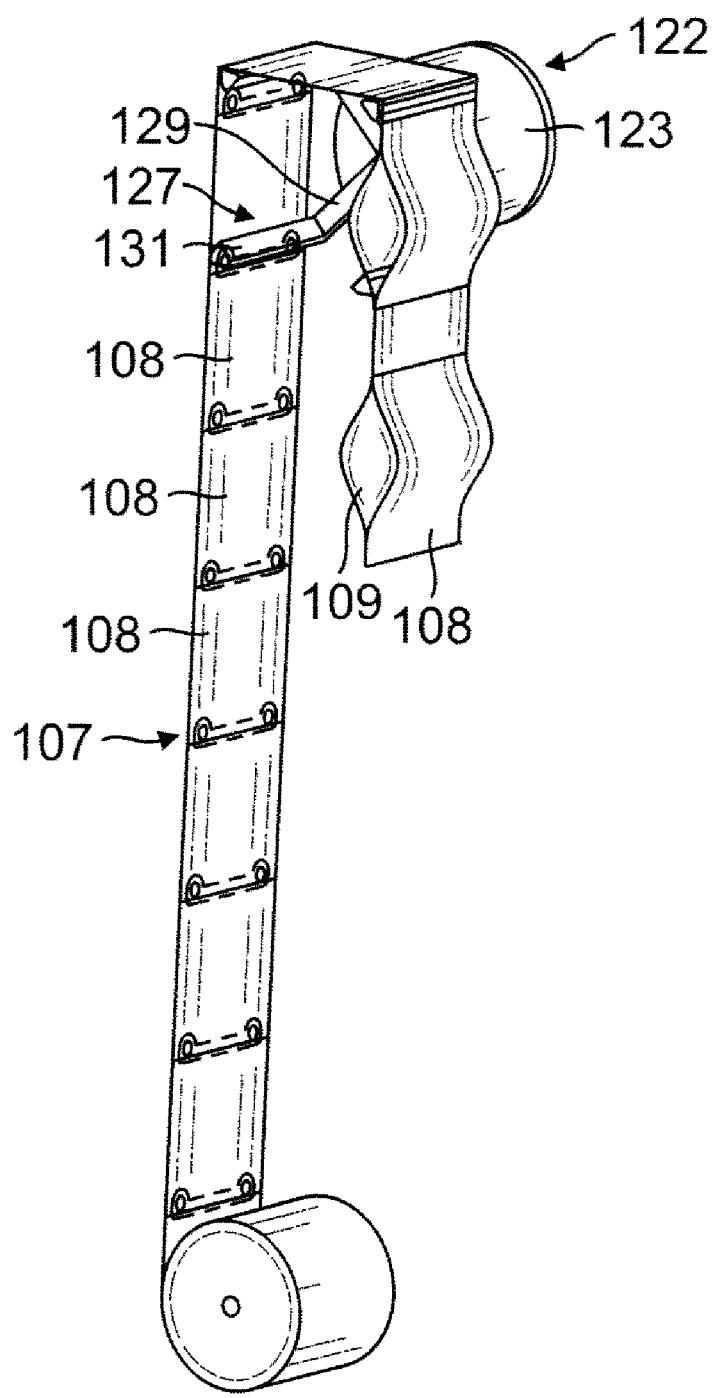

With reference now to FIGS. 11*a*, 11*b*, and 16*a*-16*c*, a bag assembly 100 comprises a bag supply 107 including a plurality of bags 108 adapted to receive and house the sample 76 provided from the loading tube 90. As shown in FIGS. 16*a*-16*c*, each bag 108 of the bag supply has first and second sheets 128, 130 sealed along two or more edges to define a space in which the sample 76 can be housed. In a stressed state as shown in, for example, FIG. 16*c*, the sheets 128, 130 have a dome shape to define a volume to allow sample 76 storage within the bag 108. However, since the bags 108 are made from a flexible synthetic polymeric material, such as polyethylene, latex, rubber, polyurethane, silicone, and/or other plastics, or from more conventional flexible materials, such as thin paper or cloth, the bags may be supplied in a relatively flat profile to ease folding or rolling for storage before use, (FIG. 11*b*). A pair of through holes 126 may be located on the bag for feeding through the bag assembly using, for example, a cogwheel arrangement that engages the holes and moves the bags such as film is moved through a projector. At least one of the sheets 128, 130 contains an opening 109 through which the sample 76 may be inserted and subsequently removed from the bag. Further, in one exemplary embodiment, the plurality of bags 108 are integrally formed and are separable at a perforated or otherwise weakened portion 124.

With reference now to FIGS. 11*a* and 11*b*, because the plurality of bags 108 of the bag assembly 107 are connected, the bag supply can be advanced to successively align a bag with the loading tube 90. In one exemplary embodiment, the bag supply 107 may be rolled about a mandrel 119 extending between vertical frame members 120 and may be extended such that the loading tube 90 can be inserted into a bag 108. A rotator assembly 122 is located on the vertical frame portion 28 to advance the bag assembly 107 to move a filled bag 108 away from the loading tube 90 and to align an empty bag with the loading tube. As shown in FIG. 11*b*, the rotator assembly 122 includes a rotor 123 for advancing the bag supply 107, the rotor having a plurality of legs 127 extending from a side surface. In one exemplary embodiment, the rotor 123 has four legs configured into an X-shape when the rotor is viewed from the side.

The legs have a first section 19 that is attached to the rotor 123 and a second section 131 extending from the first section to be generally parallel to an outer circumferential surface of the rotor and adapted to engage the bag assembly 107. The bag assembly 107 is extended around the legs 127 of the rotator assembly 122 such that rotation of the rotor 123 advances the bag assembly 107 and allows successive bags 108 to be aligned with the loading tube 90. In one exemplary embodiment, the second section 131 may comprise a gripping surface, such as rubber, to more securely grip the bag supply 107. The rotator assembly 122 mounts to the frame 26 on feet or other supports consistent with those typically supplied with the chosen rotator assembly. One of ordinary skill in the art will appreciate that other bag supply configurations may also be used to align a bag with the loading tube 90.

Figure 12:
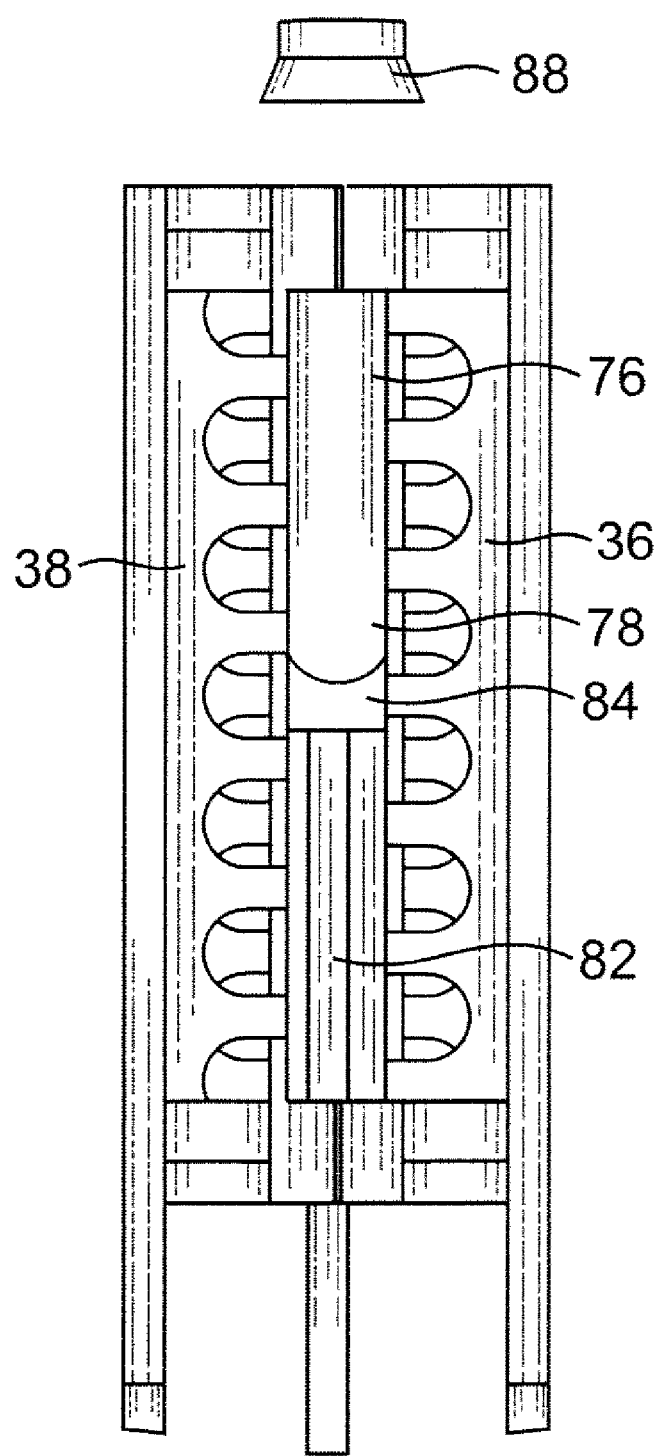
FIG. 12 is a schematic side view of an actuator rod of the bagging assembly of FIG. 10 pushing a sample into a receiving cylinder.
Figure 13:
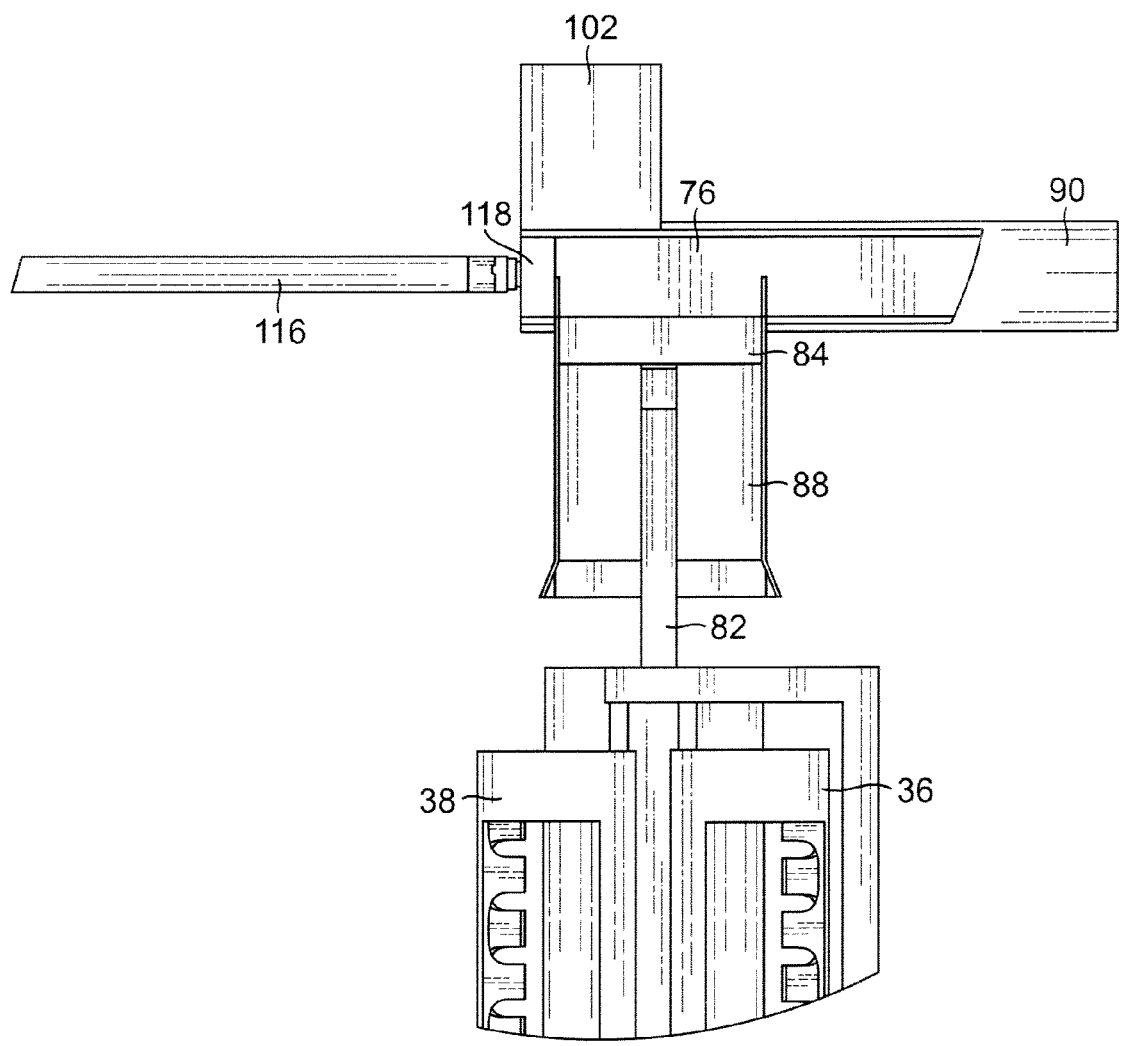
FIG. 13 is a schematic partially cutaway detail view of a sample within the loading tube of the bagging assembly of FIG. 10.
Figure 14:
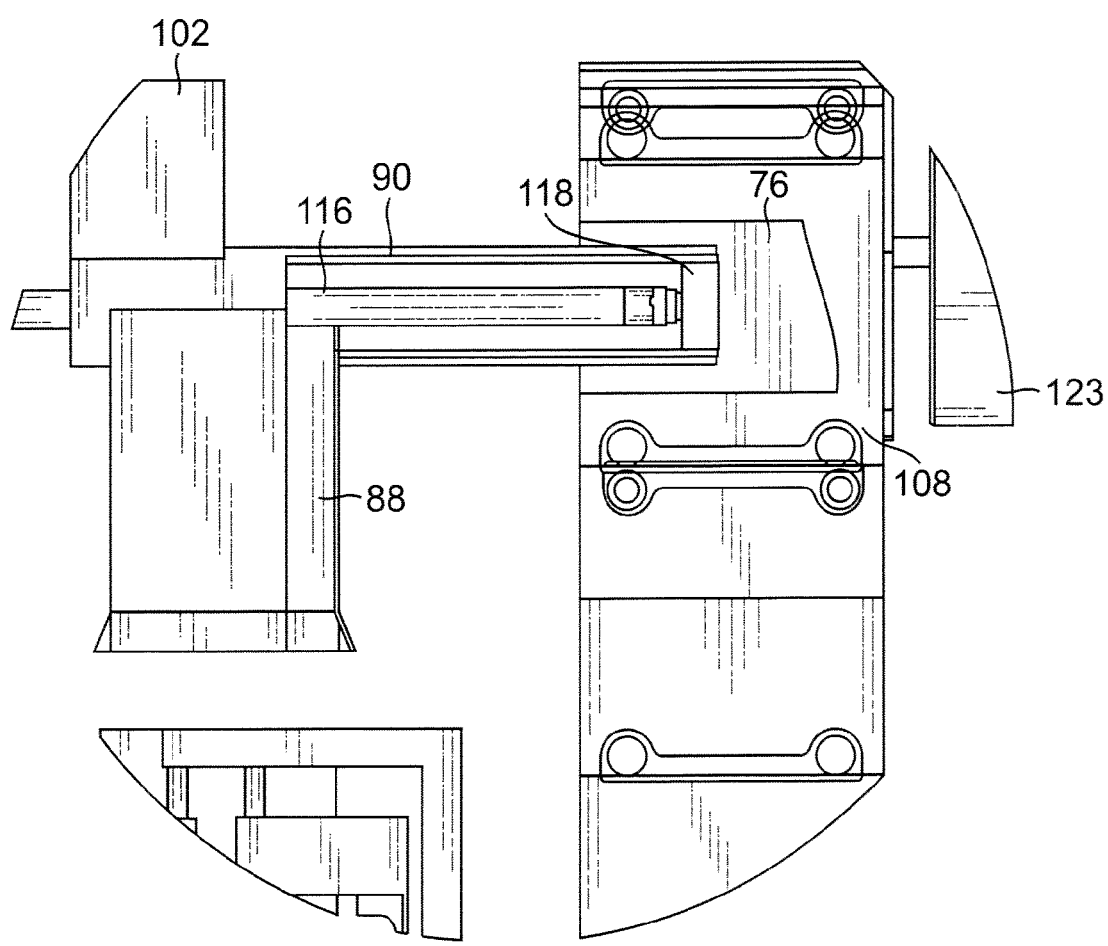
FIG. 14 is a schematic partially cutaway detail view of a sample being pushed into a bag of the bag supply of FIG. 10.

Operation of the bagging assembly 80 to bag a sample will now be described. With reference to FIG. 4 in combination with FIG. 9, the sample bays 46 of the first and second grippers 36, 38 are aligned to form the channel 78 containing the sample 76, the channel aligned with the actuator rod 82. With reference to FIGS. 12 and 13, the actuator rod 82 is advanced into the channel 78 to compress the sample 76 and push it through the receiving cylinder 88 and into the loading tube 90. As shown in FIG. 14, the loading tube actuator 112 extends the loading tube 90 into the opening 109 of a bag 108 and, once the sample 76 has been compressed into the loading tube, the loading rod actuator 114 actuates the loading rod 116 to push the sample from the loading tube 90 into the bag 108 into which the loading tube extends.

With reference now also to FIG. 15, the loading tube 90 and the extended loading head 118 then retreat, allowing the sample 76 to laterally expand within the bag 108. Due to the properties of many fibrous substances, such as cotton, once a sample 76 is laterally compressed to a certain degree, the sample will not laterally expand to a width greater than to which it has been compressed. In other words, the lateral expansion of the sample 76 is predictable and controllable, and the samples are sized such that they will not expand more than a width of the bag 108 even once the force of the loading head 118 is removed and even if the opening 109 of the bag is not sealed. After the loading tube 90 has been retracted, the rotator assembly 122 rotates to advance the bag supply 107 to align the next bag 108 with the loading tube, and the process is repeated. In another exemplary embodiment, the bags 108 may be moved relative to the loading tube 90, rather than moving the loading tube relative to the bags, to achieve the same result. In yet another embodiment, a stack of bags or a roll of bags are used and are manually fed through the system although automation is more preferred. In still yet another embodiment, a return rotator assembly (not shown) is used to roll the bags with samples into a roll so that the roll of sample bags are automatically rolled for collection or other purposes. Alternatively, the sample bags may be separated into individual bags with samples.

Figure 17:
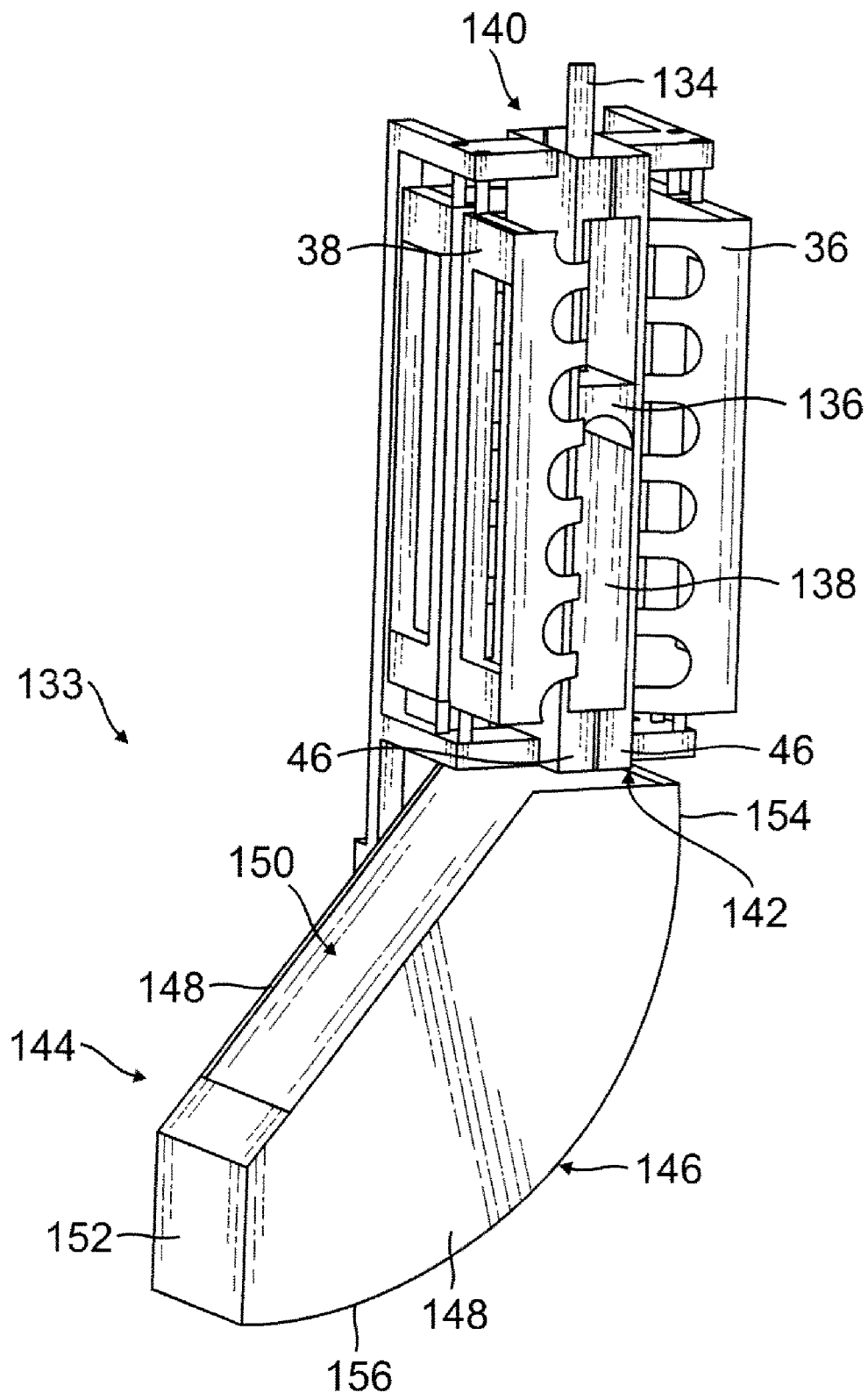
FIG. 17 is an orthogonal view of an exemplary embodiment of a manual sample collection device according to aspects of the present invention.

With reference now to FIG. 17, an alternative embodiment of the present invention is provided as a sample collector assembly 133. More specifically, first and second grippers 36, 38 are provided having a sample bay 46 for housing a sample 76, similarly to previously described embodiments. An ejection rod 134 having an ejection head 136 at a distal end thereof is adapted to slide through the channel 138 created by the sample bays 46 of the first and second grippers 36, 38 when the sample bays are abutting. As shown in FIG. 17, the ejection rod 134 is configured to enter the channel 138 from a top opening 140 and push the sample 76 out of a bottom opening 142 into a collector bin 144 from which the samples can be manually collected. In one exemplary embodiment, the collector bin 144 comprises an arcuate base wall 146 and two side walls 148 extending from the base wall 146 to form a generally U-shaped channel 150 into which the sample 76 will be pushed.

The arcuate configuration of the base wall 146 having a generally vertical section 154 near the bottom opening 142 and a generally horizontal section 156 distally from the vertical section allows the sample to slide down the base wall toward the horizontal section, where it can be easily collected. The collector bin 144 may also comprise an end wall 152 extending between the side walls 148 and base wall 146 and covering a portion of the channel 150 to prevent the sample 76 from sliding out of the collector bin. One of ordinary skill in the art will appreciate that the collector bin 144 may also have other configurations, such as an angled base wall or a flat base wall, while remaining within the spirit and scope of the present invention. In an alternatively embodiment, the ejection rod may be repositioned to push the sample upwards instead of downwards into a collector bin located above the first and second grippers 36, 38.

Figure 18:
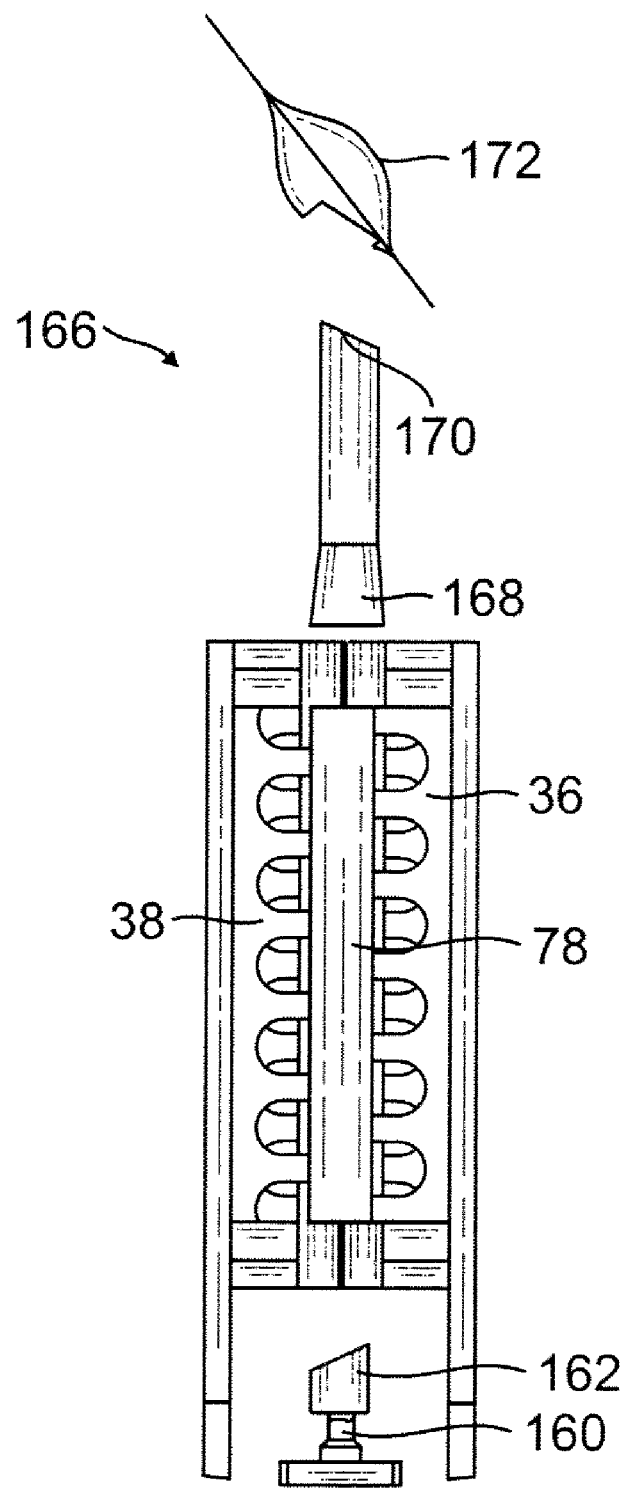

Another exemplary embodiment of the present invention is provided with reference now to FIGS. 18-19. As shown in FIG. 18, the sample bays 46 of the first and second grippers 36, 38 are abutted to form the channel 78 containing the sample 76. An ejection rod 160 having an ejection head 162 at a distal end thereof is located, in a retracted position, below a bottom opening 164 of the channel 158, the ejection rod is adapted to slide through the channel 78 to eject the sample therefrom. In one exemplary embodiment, the ejection rod 160 ejects the sample 76 into a loading tube 166 having a generally flared lower section 168 adapted to receive the sample and an angled upper opening 170 through which the sample passes into a bag 172.

The loading tube 166 is movable between a lowered position (FIG. 18), in which the flared lower section is proximate to a top opening 165 of the channel 158 and a raised position (FIG. 19), in which the angled upper opening 170 engages or is proximate an opening 174 in the bag 172. In one exemplary embodiment, a bag supply 171 (FIG. 20*a*-20*c*) supplies bags 172 from above the loading tube 166 such that a bag for receiving the sample 76 is in alignment with the loading tube 166 at about a 45 degree angle. With the loading tube 166 abutting the opening 174 of the bag 172, the ejection rod 160 with ejection head 162 will apply force to the sample 76 within the loading tube to eject the sample into the bag. As described in more detail below, due to the shape of opening and the expansion of the sample 76 within the bag 172, the sample will remain in the bag even when the loading cylinder 166 retracts to its lowered position and the opening 174 is unobstructed and facing downward. As will be appreciated, it is also feasible for an upper section of each gripper 36, 38 to be extended to form a loading tube, thus eliminating the need for a separate component.

With reference now to FIGS. 20*a*-20*e*, the bag supply 171 comprises a plurality of bags 172. Similarly to previously described embodiments, each bag 172 comprises a first side panel 176 and a second side panel 178 sealed on a plurality of edges, such as four edges, to define a space for containing the sample 76. In one exemplary embodiment, the first and second sheets 176, 178 may have a generally domed configuration when stressed to receive a sample or with a sample within. A rim 180 may extend from the sheets 176, 178, the rim including at least one through hole 182 for use to sequentially move the bags through the bagging assembly, such as a cogwheel arrangement. It will be appreciated that holes 182 may not be necessary to index the bag, in which case they would not be included. At least one of the sheets 176, 178 contains an opening 174 through which the sample 76 may be inserted into and removed from the bag. As shown in FIG. 20*c*, the opening 174 has a notched profile that allows an opening large enough to accept a sample, yet provides a cradle portion 186 that maintains a sample within the bag 172 even when the opening is facing downward and is unobstructed. Further, in one exemplary embodiment, the plurality of bags 172 are integrally formed and are separable at a perforated or otherwise weakened portion 194. In an alternative embodiment, an opening 174 is formed on each of the two sheets 176, 178 of the bag such that each bag as two openings 174. The bag may also include information materials, such as information about the sample and the bale it was taken from. The information may be provided on a sticker to be placed on the bag, on a sheet of paper to be placed inside the bag, printed on the outside of the bag, or combination thereof.

Figure 21A:
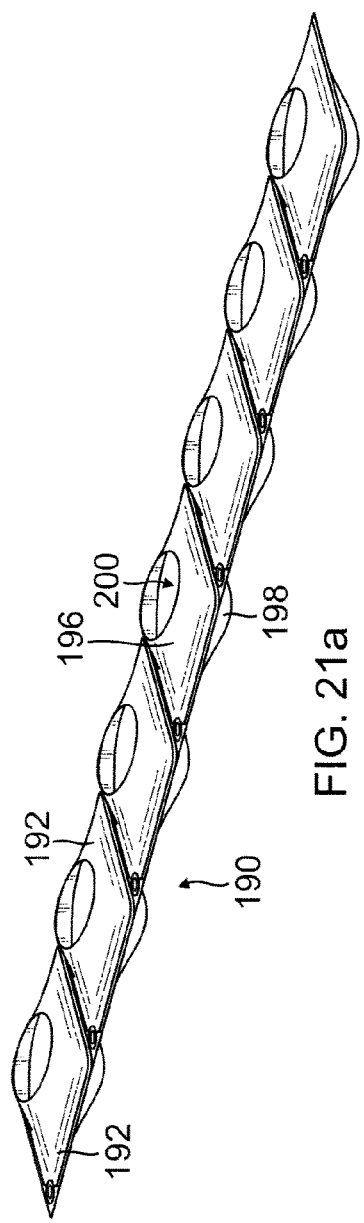
FIGS. 21a, 21b, and 21c are a top, side, and orthogonal views, respectively, of yet another exemplary bag supply in accordance with aspects of the present invention.
Figure 21B:
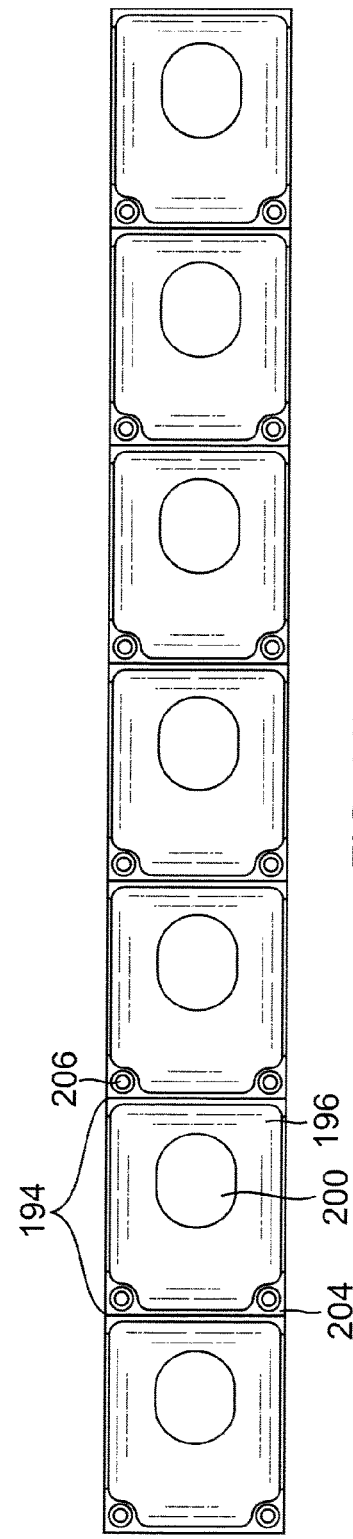
Figure 21C:
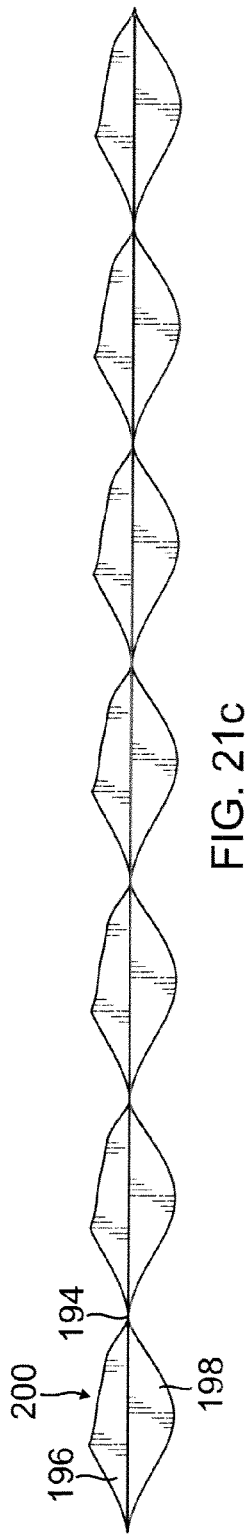

With reference now to FIGS. 21*a*-21*c*, another exemplary embodiment of a bag supply 190 is provided. Similarly to the previously described bag supplies, the bag supply 190 comprises a plurality of bags 192 integral with each other and separable along a weakened portion 194. Each bag 192 includes a first and second side panel 196, 198, at least one of the panels having an opening 200 into which a sample is insertable. As shown in FIG. 21*c*, the first and second sheets 196, 198 may be generally dome-shaped, but the opening may have an angled profile such that a cradle portion 202 is formed to allow a sample to remain in the bag 192 even when the opening 200 is unobstructed and facing downward. Further, a rim 204 may extend from the sheets 196, 198 to provide structural support for the bag 192, the rim having a pair of through holes 206 extending therethrough to allow a bag supply transport to align the bags into an appropriate position with a loading tube.

With reference now to FIGS. 22*a*-22*c*, another exemplary embodiment of a bag supply 208 comprising a plurality of bags 210 is provided, similar to the previously described bag supply embodiments. However, each bag 210 has a slot 212 into which an opening of a loading tube or other sample containing device may be inserted, and from which a sample can then be ejected into the bag.

Although limited sampling assembly embodiments have been specifically described and illustrated many modifications, combinations, and variations of the embodiments will be apparent to those skilled in the art. For example, the dimensions and positioning of the components on the frame may be modified to achieve their intended purpose. Accordingly, it is to be understood that the bale sampler constructed according to principles of this invention may be embodied other than as specifically described herein. The invention is also defined in the following claims.

What is claimed is:

1. A system for sampling a bale of fibrous material comprising:
    a support surface for supporting a bale;
    a stop surface spaced from and opposing a gripper to support against a force exerted by the gripper; the stop surface being spaced and remote from the support surface; and
    wherein the gripper comprises a movable edge configured for moving against a partially cut sample to pull the sample from the bale;
    wherein the stop surface is a second gripper configured to cooperate with the gripper; and
    wherein the second gripper and the gripper contact one another to from a channel for holding a fibrous sample.

2. The system of claim 1, further comprising
    a transportation mechanism for moving a bale from a first point to a second point adjacent the gripper.

3. The system of claim 1, further comprising a sample bay forming part of the channel, the sample bay comprising a base and a side.

4. The system of claim 1, further comprising a rotator assembly spaced from the gripper for moving bags near the gripper to collect a fibrous sample.

5. The system of claim 1, further comprising an ejector system for ejecting a fibrous sample from the channel.

6. The system of claim 1, further comprising a bag assembly comprising a plurality of bags.

7. The system of claim 1, further comprising a bag comprising seal edges and an opening for receiving a sample.

8. A system for sampling a bale of fibrous material comprising:
    a support surface for supporting a bale;
    a stop surface spaced from and opposing a gripper to support against a force exerted by the gripper; the stop surface being spaced and remote from the support surface; and wherein the gripper comprises a movable edge configured for moving against a partially cut sample to pull the sample from the bale; and wherein the movable edge comprises a plurality of spaced apart fingers comprising a plurality of spaced edges.

9. The system of claim 8, wherein the plurality of spaced apart fingers are located on a plate, which is pivotable.

10. The system of claim 8, further comprising a bag assembly comprising a plurality of bags.

11. The system of claim 10, further comprising a rotator assembly for advancing the bags.

12. The system of claim 10, further comprising a color bin comprising an open channel for receiving samples.

13. A system for sampling a bale of fibrous material comprising:
 a support surface for supporting a bale;
 a stop surface spaced from and opposing a gripper to support against a force exerted by the gripper; the stop surface being spaced and remote from the support surface; and wherein the gripper comprises a movable edge configured for moving against a partially cut sample to pull the sample from the bale; and wherein the movable edge is rotatable around a sidewall of a sample bay for gripping the cut sample.

14. The system of claim 13, wherein the movable edge comprises a plurality of spaced apart fingers comprising a plurality of spaced edges.

15. The system of claim 13, further comprising a bag assembly comprising at least one bag for collecting a bale sample.

16. The system of claim 15, further comprising a plurality of bags for collecting a plurality of samples.

17. The system of claim 15, wherein the bag comprises a first side and a second side and wherein an opening is provided on the first side or the second side.

18. The system of claim 15, further comprising a rotator assembly for advancing the at least one bag.

* * * * *